(12) United States Patent
Richard et al.

(10) Patent No.: US 11,446,035 B2
(45) Date of Patent: Sep. 20, 2022

(54) RETAINING MECHANISMS FOR TROCAR ASSEMBLIES

(71) Applicant: Covidien LP, Mansfield, MA (US)

(72) Inventors: Paul D. Richard, Shelton, CT (US); Ramiro D. Cabrera, Cheshire, CT (US); Stephen R. Paul, East Hartford, CT (US); Jonathan W. Sapienza, Orange, CT (US); David E. Valentine, Hamden, CT (US); Justin Williams, Southbury, CT (US); Anthony Sgroi, Jr., Wallingford, CT (US)

(73) Assignee: Covidien LP, Mansfield, MA (US)

( * ) Notice: Subject to any disclaimer, the term of this patent is extended or adjusted under 35 U.S.C. 154(b) by 234 days.

(21) Appl. No.: 16/814,122

(22) Filed: Mar. 10, 2020

(65) Prior Publication Data

US 2020/0397441 A1 Dec. 24, 2020

Related U.S. Application Data

(63) Continuation-in-part of application No. 16/503,838, filed on Jul. 5, 2019, now Pat. No. 11,123,101, and a
(Continued)

(51) Int. Cl.
*A61B 17/064* (2006.01)
*A61B 17/115* (2006.01)
(Continued)

(52) U.S. Cl.
CPC ... *A61B 17/1155* (2013.01); *A61B 2017/0053* (2013.01); *A61B 2017/00486* (2013.01);
(Continued)

(58) Field of Classification Search
CPC ...... A61B 17/1155; A61B 2017/00473; A61B 2017/00477
See application file for complete search history.

(56) References Cited

U.S. PATENT DOCUMENTS

| 2,957,353 A | 10/1960 | Babacz |
| 3,111,328 A | 11/1963 | Di Rito et al. |

(Continued)

FOREIGN PATENT DOCUMENTS

| CA | 908529 A | 8/1972 |
| CA | 2451558 A1 | 1/2003 |

(Continued)

OTHER PUBLICATIONS

Extended European Search Report corresponding to International Application No. EP 14 18 4882.0 dated May 12, 2015.
(Continued)

*Primary Examiner* — Eyamindae C Jallow
(74) *Attorney, Agent, or Firm* — Carter, DeLuca & Farrell LLP

(57) ABSTRACT

An adapter assembly for connecting a loading unit to a handle assembly includes a sleeve, a trocar assembly releasably securable with the sleeve, and a retaining mechanism configured to releasably secure the trocar assembly within the sleeve and to facilitate cleaning and sterilizing of the adapter assembly. The retaining mechanism includes first and second button members and a mechanism for maintaining the first and second button members relative to each other.

20 Claims, 14 Drawing Sheets

Related U.S. Application Data continuation-in-part of application No. 16/503,726, filed on Jul. 5, 2019, and a continuation-in-part of application No. 16/449,614, filed on Jun. 24, 2019.

(51) Int. Cl.
  *A61B 17/00* (2006.01)
  *A61B 17/072* (2006.01)

(52) U.S. Cl.
  CPC ............ *A61B 2017/07257* (2013.01); *A61B 2017/07271* (2013.01)

(56) References Cited

U.S. PATENT DOCUMENTS

| | | | |
|---|---|---|---|
| 3,193,165 A | 7/1965 | Akhalaya et al. |
| 3,388,847 A | 6/1968 | Kasulin et al. |
| 3,552,626 A | 1/1971 | Astafiev et al. |
| 3,638,652 A | 2/1972 | Kelley |
| 3,695,058 A | 10/1972 | Keith, Jr. |
| 3,734,515 A | 5/1973 | Dudek |
| 3,759,336 A | 9/1973 | Marcovitz et al. |
| 3,771,526 A | 11/1973 | Rudie |
| 4,162,399 A | 7/1979 | Hudson |
| 4,198,982 A | 4/1980 | Fortner et al. |
| 4,207,898 A | 6/1980 | Becht |
| 4,289,133 A | 9/1981 | Rothfuss |
| 4,304,236 A | 12/1981 | Conta et al. |
| 4,319,576 A | 3/1982 | Rothfuss |
| 4,350,160 A | 9/1982 | Kolesov et al. |
| 4,351,466 A | 9/1982 | Noiles |
| 4,379,457 A | 4/1983 | Gravener et al. |
| 4,473,077 A | 9/1984 | Noiles et al. |
| 4,476,863 A | 10/1984 | Kanshln et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,520,817 A | 6/1985 | Green |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,632,290 A | 12/1986 | Green et al. |
| 4,646,745 A | 3/1987 | Noiles |
| 4,665,917 A | 5/1987 | Clanton et al. |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,705,038 A | 11/1987 | Sjostrom et al. |
| 4,708,141 A | 11/1987 | Inoue et al. |
| 4,717,063 A | 1/1988 | Ebihara |
| 4,722,685 A | 2/1988 | de Estrada et al. |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,823,807 A | 4/1989 | Russell et al. |
| 4,873,977 A | 10/1989 | Avant et al. |
| 4,874,181 A | 10/1989 | Hsu |
| 4,893,662 A | 1/1990 | Gervasi |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 4,962,877 A | 10/1990 | Hervas |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,129,118 A | 7/1992 | Walmesley |
| 5,129,570 A | 7/1992 | Schulze et al. |
| 5,139,513 A | 8/1992 | Segato |
| 5,152,744 A | 10/1992 | Krause et al. |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A | 12/1993 | Grant et al. |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,301,061 A | 4/1994 | Nakada et al. |
| 5,309,927 A | 5/1994 | Welch |
| 5,312,023 A | 5/1994 | Green et al. |
| 5,312,024 A | 5/1994 | Grant et al. |
| 5,314,435 A | 5/1994 | Green et al. |
| 5,314,436 A | 5/1994 | Wilk |
| 5,326,013 A | 7/1994 | Green et al. |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A | 9/1994 | Blanco et al. |
| 5,350,104 A | 9/1994 | Main et al. |
| 5,350,355 A | 9/1994 | Sklar |
| 5,355,897 A | 10/1994 | Pietrafitta et al. |
| 5,360,154 A | 11/1994 | Green |
| 5,368,215 A | 11/1994 | Green et al. |
| 5,383,874 A | 1/1995 | Jackson et al. |
| 5,383,880 A | 1/1995 | Hooven |
| 5,389,098 A | 2/1995 | Tsuruta et al. |
| 5,392,979 A | 2/1995 | Green et al. |
| 5,395,030 A | 3/1995 | Kuramoto et al. |
| 5,395,033 A | 3/1995 | Byrne et al. |
| 5,400,267 A | 3/1995 | Denen et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,413,267 A | 5/1995 | Solyntjes et al. |
| 5,425,738 A | 6/1995 | Gustafson et al. |
| 5,427,087 A | 6/1995 | Ito et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,447,514 A | 9/1995 | Gerry et al. |
| 5,454,825 A | 10/1995 | Van Leeuwen et al. |
| 5,464,415 A | 11/1995 | Chen |
| 5,467,911 A | 11/1995 | Tsuruta et al. |
| 5,470,006 A | 11/1995 | Rodak |
| 5,474,223 A | 12/1995 | Viola et al. |
| 5,476,379 A | 12/1995 | Disel |
| 5,487,499 A | 1/1996 | Sorrentino et al. |
| 5,497,934 A | 3/1996 | Brady et al. |
| 5,503,635 A | 4/1996 | Sauer et al. |
| 5,518,163 A | 5/1996 | Hooven |
| 5,518,164 A | 5/1996 | Hooven |
| 5,522,534 A | 6/1996 | Viola et al. |
| 5,526,822 A | 6/1996 | Burbank et al. |
| 5,529,235 A | 6/1996 | Boiarski et al. |
| 5,533,661 A | 7/1996 | Main et al. |
| 5,535,934 A | 7/1996 | Boiarski et al. |
| 5,535,937 A | 7/1996 | Boiarski et al. |
| 5,540,375 A | 7/1996 | Bolanos et al. |
| 5,540,706 A | 7/1996 | Aust et al. |
| 5,542,594 A | 8/1996 | McKean et al. |
| 5,549,637 A | 8/1996 | Crainich |
| 5,553,675 A | 9/1996 | Pitzen et al. |
| 5,562,239 A | 10/1996 | Boiarski et al. |

(56) References Cited

U.S. PATENT DOCUMENTS

| | | |
|---|---|---|
| 5,564,615 A | 10/1996 | Bishop et al. |
| 5,588,579 A | 12/1996 | Schnut et al. |
| 5,609,285 A | 3/1997 | Grant et al. |
| 5,609,560 A | 3/1997 | Ichikawa et al. |
| 5,626,587 A | 5/1997 | Bishop et al. |
| 5,626,591 A | 5/1997 | Kockerling et al. |
| 5,632,432 A | 5/1997 | Schulze et al. |
| 5,632,433 A | 5/1997 | Grant et al. |
| 5,639,008 A | 6/1997 | Gallagher et al. |
| 5,641,111 A | 6/1997 | Ahrens et al. |
| 5,645,209 A | 7/1997 | Green et al. |
| 5,647,526 A | 7/1997 | Green et al. |
| 5,653,374 A | 8/1997 | Young et al. |
| 5,658,300 A | 8/1997 | Bito et al. |
| 5,662,662 A | 9/1997 | Bishop et al. |
| 5,667,517 A | 9/1997 | Hooven |
| 5,669,918 A | 9/1997 | Balazs et al. |
| 5,685,474 A | 11/1997 | Seeber |
| 5,693,042 A | 12/1997 | Boiarski et al. |
| 5,704,534 A | 1/1998 | Huitema et al. |
| 5,709,335 A | 1/1998 | Heck |
| 5,713,505 A | 2/1998 | Huitema |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,749,896 A | 5/1998 | Cook |
| 5,758,814 A | 6/1998 | Gallagher et al. |
| 5,762,603 A | 6/1998 | Thompson |
| 5,779,130 A | 7/1998 | Alesi et al. |
| 5,782,396 A | 7/1998 | Mastri et al. |
| 5,782,397 A | 7/1998 | Koukline |
| 5,792,573 A | 8/1998 | Pitzen et al. |
| 5,797,536 A | 8/1998 | Smith et al. |
| 5,799,857 A | 9/1998 | Robertson et al. |
| 5,814,055 A | 9/1998 | Knodel et al. |
| 5,820,009 A | 10/1998 | Melling et al. |
| 5,833,698 A | 11/1998 | Hinchliffe et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,863,159 A | 1/1999 | Lasko |
| 5,868,760 A | 2/1999 | McGuckin, Jr. |
| 5,881,943 A | 3/1999 | Heck et al. |
| 5,908,427 A | 6/1999 | McKean et al. |
| 5,915,616 A | 6/1999 | Viola et al. |
| 5,947,363 A | 9/1999 | Bolduc et al. |
| 5,951,576 A | 9/1999 | Wakabayashi |
| 5,954,259 A | 9/1999 | Viola et al. |
| 5,957,363 A | 9/1999 | Heck |
| 5,964,774 A | 10/1999 | McKean et al. |
| 5,993,454 A | 11/1999 | Longo |
| 5,993,468 A | 11/1999 | Rygaard |
| 6,010,054 A | 1/2000 | Johnson et al. |
| 6,017,354 A | 1/2000 | Culp et al. |
| 6,024,748 A | 2/2000 | Manzo et al. |
| 6,032,849 A | 3/2000 | Mastri et al. |
| 6,045,560 A | 4/2000 | McKean et al. |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,090,123 A | 7/2000 | Culp et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,126,651 A | 10/2000 | Mayer |
| 6,129,547 A | 10/2000 | Cise et al. |
| 6,142,933 A | 11/2000 | Longo et al. |
| 6,149,667 A | 11/2000 | Hovland et al. |
| 6,165,169 A | 12/2000 | Panescu et al. |
| 6,176,413 B1 | 1/2001 | Heck et al. |
| 6,179,195 B1 | 1/2001 | Adams et al. |
| 6,193,129 B1 | 2/2001 | Bittner et al. |
| 6,203,553 B1 | 3/2001 | Robertson et al. |
| 6,209,773 B1 | 4/2001 | Bolduc et al. |
| 6,239,732 B1 | 5/2001 | Cusey |
| 6,241,139 B1 | 6/2001 | Milliman et al. |
| 6,241,140 B1 | 6/2001 | Adams et al. |
| 6,253,984 B1 | 7/2001 | Heck et al. |
| 6,258,107 B1 | 7/2001 | Balazs et al. |
| 6,264,086 B1 | 7/2001 | McGuckin, Jr. |
| 6,264,087 B1 | 7/2001 | Whitman |
| 6,269,997 B1 | 8/2001 | Balazs et al. |
| 6,273,897 B1 | 8/2001 | Dalessandro et al. |
| 6,279,809 B1 | 8/2001 | Nicolo |
| 6,302,311 B1 | 10/2001 | Adams et al. |
| 6,315,184 B1 | 11/2001 | Whitman |
| 6,321,855 B1 | 11/2001 | Barnes |
| 6,329,778 B1 | 12/2001 | Culp et al. |
| 6,338,737 B1 | 1/2002 | Toledano |
| 6,343,731 B1 | 2/2002 | Adams et al. |
| 6,348,061 B1 | 2/2002 | Whitman |
| 6,368,324 B1 | 4/2002 | Dinger et al. |
| 6,371,909 B1 | 4/2002 | Hoeg et al. |
| 6,387,105 B1 | 5/2002 | Gifford, III et al. |
| 6,398,795 B1 | 6/2002 | McAlister et al. |
| 6,402,008 B1 | 6/2002 | Lucas |
| 6,434,507 B1 | 8/2002 | Clayton et al. |
| 6,439,446 B1 | 8/2002 | Perry et al. |
| 6,443,973 B1 | 9/2002 | Whitman |
| 6,450,390 B2 | 9/2002 | Heck et al. |
| 6,461,372 B1 | 10/2002 | Jensen et al. |
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,537,280 B2 | 3/2003 | Dinger et al. |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,610,066 B2 | 8/2003 | Dinger et al. |
| 6,611,793 B1 | 8/2003 | Burnside et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,645,218 B1 | 11/2003 | Cassidy et al. |
| 6,652,542 B2 | 11/2003 | Blatter et al. |
| 6,654,999 B2 | 12/2003 | Stoddard et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,699,177 B1 | 3/2004 | Wang et al. |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,240 B2 | 6/2004 | Smith et al. |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,783,533 B2 | 8/2004 | Green et al. |
| 6,792,390 B1 | 9/2004 | Burnside et al. |
| 6,793,652 B1 | 9/2004 | Whitman et al. |
| 6,817,508 B1 | 11/2004 | Racenet et al. |
| 6,820,791 B2 | 11/2004 | Adams |

(56) References Cited

U.S. PATENT DOCUMENTS

| | | | |
|---|---|---|---|
| 6,821,282 B2 | 11/2004 | Perry et al. |
| 6,827,246 B2 | 12/2004 | Sullivan et al. |
| 6,830,174 B2 | 12/2004 | Hillstead et al. |
| 6,840,423 B2 | 1/2005 | Adams et al. |
| 6,843,403 B2 | 1/2005 | Whitman |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,852,122 B2 | 2/2005 | Rush |
| 6,860,892 B1 | 3/2005 | Tanaka et al. |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,899,538 B2 | 5/2005 | Matoba |
| 6,905,057 B2 | 6/2005 | Swayze et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2 | 11/2005 | Heinrich |
| 6,959,852 B2 | 11/2005 | Shelton, IV et al. |
| 6,964,363 B2 | 11/2005 | Wales et al. |
| 6,978,922 B2 | 12/2005 | Bilotti et al. |
| 6,981,628 B2 | 1/2006 | Wales |
| 6,981,941 B2 | 1/2006 | Whitman et al. |
| 6,981,979 B2 | 1/2006 | Nicolo |
| 6,986,451 B1 | 1/2006 | Mastri et al. |
| 6,988,649 B2 | 1/2006 | Shelton, IV et al. |
| 7,032,798 B2 | 4/2006 | Whitman et al. |
| RE39,152 E | 6/2006 | Aust et al. |
| 7,055,731 B2 | 6/2006 | Shelton, IV et al. |
| 7,059,331 B2 | 6/2006 | Adams et al. |
| 7,059,508 B2 | 6/2006 | Shelton, IV et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,111,769 B2 | 9/2006 | Wales et al. |
| 7,114,642 B2 | 10/2006 | Whitman |
| 7,118,528 B1 | 10/2006 | Piskun |
| 7,122,029 B2 | 10/2006 | Koop et al. |
| 7,122,044 B2 | 10/2006 | Bolduc et al. |
| 7,128,748 B2 | 10/2006 | Mooradian et al. |
| 7,140,528 B2 | 11/2006 | Shelton, IV |
| 7,141,049 B2 | 11/2006 | Stern et al. |
| 7,141,055 B2 | 11/2006 | Abrams et al. |
| 7,143,923 B2 | 12/2006 | Shelton, IV et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,168,604 B2 | 1/2007 | Milliman et al. |
| 7,172,104 B2 | 2/2007 | Scirica et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,220,237 B2 | 5/2007 | Gannoe et al. |
| 7,225,964 B2 | 6/2007 | Mastri et al. |
| 7,234,624 B2 | 6/2007 | Gresham et al. |
| 7,235,089 B1 | 6/2007 | McGuckin, Jr. |
| 7,238,021 B1 | 7/2007 | Johnson |
| 7,246,734 B2 | 7/2007 | Shelton, IV |
| 7,252,660 B2 | 8/2007 | Kunz |
| RE39,841 E | 9/2007 | Bilotti et al. |
| 7,285,125 B2 | 10/2007 | Viola |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,328,828 B2 | 2/2008 | Ortiz et al. |
| 7,334,718 B2 | 2/2008 | McAlister et al. |
| 7,335,212 B2 | 2/2008 | Edoga et al. |
| 7,364,060 B2 | 4/2008 | Milliman |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,404,508 B2 | 7/2008 | Smith et al. |
| 7,407,075 B2 | 8/2008 | Holsten et al. |
| 7,407,078 B2 | 8/2008 | Shelton, IV et al. |
| 7,410,086 B2 | 8/2008 | Ortiz et al. |
| 7,416,101 B2 | 8/2008 | Shelton, IV et al. |
| 7,419,080 B2 | 9/2008 | Smith et al. |
| 7,422,137 B2 | 9/2008 | Manzo |
| 7,422,138 B2 | 9/2008 | Bilotti et al. |
| 7,422,139 B2 | 9/2008 | Shelton, IV et al. |
| 7,431,189 B2 | 10/2008 | Shelton, IV et al. |
| 7,431,191 B2 | 10/2008 | Milliman |
| 7,438,718 B2 | 10/2008 | Milliman et al. |
| 7,441,684 B2 | 10/2008 | Shelton, IV et al. |
| 7,448,525 B2 | 11/2008 | Shelton, IV et al. |
| 7,455,676 B2 | 11/2008 | Holsten et al. |
| 7,455,682 B2 | 11/2008 | Viola |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,481,347 B2 | 1/2009 | Roy |
| 7,481,824 B2 | 1/2009 | Boudreaux et al. |
| 7,487,899 B2 | 2/2009 | Shelton, IV et al. |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,546,939 B2 | 6/2009 | Adams et al. |
| 7,546,940 B2 | 6/2009 | Milliman et al. |
| 7,547,312 B2 | 6/2009 | Bauman et al. |
| 7,549,564 B2 | 6/2009 | Boudreaux |
| 7,556,186 B2 | 7/2009 | Milliman |
| 7,559,451 B2 | 7/2009 | Sharma et al. |
| 7,565,993 B2 | 7/2009 | Milliman et al. |
| 7,568,603 B2 | 8/2009 | Shelton, IV et al. |
| 7,575,144 B2 | 8/2009 | Ortiz et al. |
| 7,585,306 B2 | 9/2009 | Abbott et al. |
| 7,588,174 B2 | 9/2009 | Holsten et al. |
| 7,588,175 B2 | 9/2009 | Timm et al. |
| 7,588,176 B2 | 9/2009 | Timm et al. |
| 7,600,663 B2 | 10/2009 | Green |
| 7,611,038 B2 | 11/2009 | Racenet et al. |
| 7,635,385 B2 | 12/2009 | Milliman et al. |
| 7,637,409 B2 | 12/2009 | Marczyk |
| 7,641,093 B2 | 1/2010 | Doll et al. |
| 7,644,848 B2 | 1/2010 | Swayze et al. |
| 7,669,747 B2 | 3/2010 | Weisenburgh, II et al. |
| 7,670,334 B2 | 3/2010 | Hueil et al. |
| 7,673,780 B2 | 3/2010 | Shelton, IV et al. |
| 7,686,201 B2 | 3/2010 | Csiky |
| 7,694,864 B2 | 4/2010 | Okada et al. |
| 7,699,204 B2 | 4/2010 | Viola |
| 7,699,835 B2 | 4/2010 | Lee et al. |
| 7,708,181 B2 | 5/2010 | Cole et al. |
| 7,717,313 B2 | 5/2010 | Criscuolo et al. |
| 7,721,931 B2 | 5/2010 | Shelton, IV et al. |
| 7,721,932 B2 | 5/2010 | Cole et al. |
| 7,726,539 B2 | 6/2010 | Holsten et al. |
| 7,738,971 B2 | 6/2010 | Swayze et al. |
| 7,740,159 B2 | 6/2010 | Shelton, IV et al. |
| 7,743,958 B2 | 6/2010 | Orban, III |
| 7,743,960 B2 | 6/2010 | Whitman et al. |
| 7,744,627 B2 | 6/2010 | Orban, III et al. |
| 7,758,613 B2 | 7/2010 | Whitman |
| 7,766,210 B2 | 8/2010 | Shelton, IV et al. |
| 7,770,773 B2 | 8/2010 | Whitman et al. |
| 7,770,775 B2 | 8/2010 | Shelton, IV et al. |
| 7,770,776 B2 | 8/2010 | Chen et al. |
| 7,771,440 B2 | 8/2010 | Ortiz et al. |
| 7,776,060 B2 | 8/2010 | Mooradian et al. |

(56) References Cited

U.S. PATENT DOCUMENTS

| | | |
|---|---|---|
| 7,793,812 B2 | 9/2010 | Moore et al. |
| 7,793,813 B2 | 9/2010 | Bettuchi |
| 7,799,039 B2 | 9/2010 | Shelton, IV et al. |
| 7,802,712 B2 | 9/2010 | Milliman et al. |
| 7,803,151 B2 | 9/2010 | Whitman |
| 7,822,458 B2 | 10/2010 | Webster, III et al. |
| 7,823,592 B2 | 11/2010 | Bettuchi et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,534 B2 | 12/2010 | Viola et al. |
| 7,845,536 B2 | 12/2010 | Viola et al. |
| 7,845,537 B2 | 12/2010 | Shelton, IV et al. |
| 7,845,538 B2 | 12/2010 | Whitman |
| 7,857,185 B2 | 12/2010 | Swayze et al. |
| 7,857,187 B2 | 12/2010 | Milliman |
| 7,870,989 B2 | 1/2011 | Viola et al. |
| 7,886,951 B2 | 2/2011 | Hessler |
| 7,896,215 B2 | 3/2011 | Adams et al. |
| 7,900,805 B2 | 3/2011 | Shelton, IV et al. |
| 7,900,806 B2 | 3/2011 | Chen et al. |
| 7,905,897 B2 | 3/2011 | Whitman et al. |
| 7,909,039 B2 | 3/2011 | Hur |
| 7,909,219 B2 | 3/2011 | Cole et al. |
| 7,909,222 B2 | 3/2011 | Cole et al. |
| 7,909,223 B2 | 3/2011 | Cole et al. |
| 7,913,892 B2 | 3/2011 | Cole et al. |
| 7,918,230 B2 | 4/2011 | Whitman et al. |
| 7,918,377 B2 | 4/2011 | Measamer et al. |
| 7,922,061 B2 | 4/2011 | Shelton, IV et al. |
| 7,922,062 B2 | 4/2011 | Cole et al. |
| 7,922,719 B2 | 4/2011 | Ralph et al. |
| 7,922,743 B2 | 4/2011 | Heinrich et al. |
| 7,931,183 B2 | 4/2011 | Orban, III |
| 7,938,307 B2 | 5/2011 | Bettuchi |
| 7,942,302 B2 | 5/2011 | Roby et al. |
| 7,947,034 B2 | 5/2011 | Whitman |
| 7,951,071 B2 | 5/2011 | Whitman et al. |
| 7,951,166 B2 | 5/2011 | Orban, III et al. |
| 7,954,682 B2 | 6/2011 | Giordano et al. |
| 7,959,050 B2 | 6/2011 | Smith et al. |
| 7,959,051 B2 | 6/2011 | Smith et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,967,181 B2 | 6/2011 | Viola et al. |
| 7,975,895 B2 | 7/2011 | Milliman |
| 7,992,758 B2 | 8/2011 | Whitman et al. |
| 8,002,795 B2 | 8/2011 | Beetel |
| 8,006,701 B2 | 8/2011 | Bilotti et al. |
| 8,006,889 B2 | 8/2011 | Adams et al. |
| 8,011,550 B2 | 9/2011 | Aranyi et al. |
| 8,011,551 B2 | 9/2011 | Marczyk et al. |
| 8,011,554 B2 | 9/2011 | Milliman |
| 8,016,177 B2 | 9/2011 | Bettuchi et al. |
| 8,016,178 B2 | 9/2011 | Olson et al. |
| 8,016,855 B2 | 9/2011 | Whitman et al. |
| 8,016,858 B2 | 9/2011 | Whitman |
| 8,020,741 B2 | 9/2011 | Cole et al. |
| 8,020,743 B2 | 9/2011 | Shelton, IV |
| 8,025,199 B2 | 9/2011 | Whitman et al. |
| 8,028,885 B2 | 10/2011 | Smith et al. |
| 8,035,487 B2 | 10/2011 | Malackowski |
| 8,038,046 B2 | 10/2011 | Smith et al. |
| 8,043,207 B2 | 10/2011 | Adams |
| 8,052,024 B2 | 11/2011 | Viola et al. |
| 8,066,167 B2 | 11/2011 | Measamer et al. |
| 8,066,169 B2 | 11/2011 | Viola |
| 8,070,035 B2 | 12/2011 | Holsten et al. |
| 8,070,037 B2 | 12/2011 | Csiky |
| 8,096,458 B2 | 1/2012 | Hessler |
| 8,109,426 B2 | 2/2012 | Milliman et al. |
| 8,109,427 B2 | 2/2012 | Orban, III |
| 8,113,406 B2 | 2/2012 | Holsten et al. |
| 8,113,407 B2 | 2/2012 | Holsten et al. |
| 8,114,118 B2 | 2/2012 | Knodel et al. |
| 8,123,103 B2 | 2/2012 | Milliman |
| 8,127,975 B2 | 3/2012 | Olson et al. |
| 8,128,645 B2 | 3/2012 | Sonnenschein et al. |
| 8,132,703 B2 | 3/2012 | Milliman et al. |
| 8,132,705 B2 | 3/2012 | Viola et al. |
| 8,136,712 B2 | 3/2012 | Zingman |
| 8,146,790 B2 | 4/2012 | Milliman |
| 8,146,791 B2 | 4/2012 | Bettuchi et al. |
| 8,152,516 B2 | 4/2012 | Harvey et al. |
| 8,157,150 B2 | 4/2012 | Viola et al. |
| 8,157,151 B2 | 4/2012 | Ingmanson et al. |
| 8,181,838 B2 | 5/2012 | Milliman et al. |
| 8,182,494 B1 | 5/2012 | Yencho et al. |
| 8,186,555 B2 | 5/2012 | Shelton, IV et al. |
| 8,186,587 B2 | 5/2012 | Zmood et al. |
| 8,192,460 B2 | 6/2012 | Orban, III et al. |
| 8,201,720 B2 | 6/2012 | Hessler |
| 8,203,782 B2 | 6/2012 | Brueck et al. |
| 8,211,130 B2 | 7/2012 | Viola |
| 8,220,367 B2 | 7/2012 | Hsu |
| 8,225,799 B2 | 7/2012 | Bettuchi |
| 8,225,981 B2 | 7/2012 | Criscuolo et al. |
| 8,231,041 B2 | 7/2012 | Marczyk et al. |
| 8,231,042 B2 | 7/2012 | Hessler et al. |
| 8,235,273 B2 | 8/2012 | Olson et al. |
| 8,241,322 B2 | 8/2012 | Whitman et al. |
| 8,257,391 B2 | 9/2012 | Orban, III et al. |
| 8,267,301 B2 | 9/2012 | Milliman et al. |
| 8,272,552 B2 | 9/2012 | Holsten et al. |
| 8,272,554 B2 | 9/2012 | Whitman et al. |
| 8,276,802 B2 | 10/2012 | Kostrzewski |
| 8,281,975 B2 | 10/2012 | Criscuolo et al. |
| 8,286,845 B2 | 10/2012 | Perry et al. |
| 8,292,150 B2 | 10/2012 | Bryant |
| 8,292,888 B2 | 10/2012 | Whitman |
| 8,308,045 B2 | 11/2012 | Bettuchi et al. |
| 8,312,885 B2 | 11/2012 | Bettuchi et al. |
| 8,313,014 B2 | 11/2012 | Bettuchi |
| 8,317,073 B2 | 11/2012 | Milliman et al. |
| 8,317,074 B2 | 11/2012 | Ortiz et al. |
| 8,322,590 B2 | 12/2012 | Patel et al. |
| 8,328,060 B2 | 12/2012 | Jankowski et al. |
| 8,328,062 B2 | 12/2012 | Viola |
| 8,328,063 B2 | 12/2012 | Milliman et al. |
| 8,342,379 B2 | 1/2013 | Whitman et al. |
| 8,343,185 B2 | 1/2013 | Milliman et al. |
| 8,348,130 B2 | 1/2013 | Shah et al. |
| 8,348,855 B2 | 1/2013 | Hillely et al. |
| 8,353,438 B2 | 1/2013 | Baxter, III et al. |
| 8,353,439 B2 | 1/2013 | Baxter, III et al. |
| 8,353,440 B2 | 1/2013 | Whitman et al. |
| 8,353,930 B2 | 1/2013 | Heinrich et al. |
| 8,357,144 B2 | 1/2013 | Whitman et al. |
| 8,360,295 B2 | 1/2013 | Milliman et al. |
| 8,365,633 B2 | 2/2013 | Simaan et al. |
| 8,365,972 B2 | 2/2013 | Aranyi et al. |
| 8,365,974 B2 | 2/2013 | Milliman |
| 8,371,492 B2 | 2/2013 | Aranyi et al. |
| 8,372,057 B2 | 2/2013 | Cude et al. |
| 8,391,957 B2 | 3/2013 | Carlson et al. |
| 8,403,926 B2 | 3/2013 | Nobis et al. |
| 8,403,942 B2 | 3/2013 | Milliman et al. |
| 8,408,441 B2 | 4/2013 | Wenchell et al. |
| 8,413,870 B2 | 4/2013 | Pastorelli et al. |
| 8,413,872 B2 | 4/2013 | Patel |
| 8,418,904 B2 | 4/2013 | Wenchell et al. |
| 8,418,905 B2 | 4/2013 | Milliman |
| 8,418,909 B2 | 4/2013 | Kostrzewski |
| 8,424,535 B2 | 4/2013 | Hessler et al. |
| 8,424,739 B2 | 4/2013 | Racenet et al. |
| 8,424,741 B2 | 4/2013 | McGuckin, Jr. et al. |
| 8,430,291 B2 | 4/2013 | Heinrich et al. |
| 8,430,292 B2 | 4/2013 | Patel et al. |
| 8,453,910 B2 | 6/2013 | Bettuchi et al. |
| 8,453,911 B2 | 6/2013 | Milliman et al. |
| 8,454,585 B2 | 6/2013 | Whitman |
| 8,485,414 B2 | 7/2013 | Criscuolo et al. |
| 8,490,853 B2 | 7/2013 | Criscuolo et al. |

(56) References Cited

U.S. PATENT DOCUMENTS

| | | | |
|---|---|---|---|
| 8,505,802 B2 | 8/2013 | Viola et al. |
| 8,511,533 B2 | 8/2013 | Viola et al. |
| 8,517,241 B2 | 8/2013 | Nicholas et al. |
| 8,523,043 B2 | 9/2013 | Ullrich et al. |
| 8,551,076 B2 | 10/2013 | Duval et al. |
| 8,551,138 B2 | 10/2013 | Orban, III et al. |
| 8,561,871 B2 | 10/2013 | Rajappa et al. |
| 8,561,874 B2 | 10/2013 | Scirica |
| 8,567,655 B2 | 10/2013 | Nalagatla et al. |
| 8,579,178 B2 | 11/2013 | Holsten et al. |
| 8,590,763 B2 | 11/2013 | Milliman |
| 8,590,764 B2 | 11/2013 | Hartwick et al. |
| 8,602,287 B2 | 12/2013 | Yates et al. |
| 8,608,047 B2 | 12/2013 | Holsten et al. |
| 8,616,428 B2 | 12/2013 | Milliman et al. |
| 8,616,429 B2 | 12/2013 | Viola |
| 8,622,275 B2 | 1/2014 | Baxter, III et al. |
| 8,623,000 B2 | 1/2014 | Humayun et al. |
| 8,627,995 B2 | 1/2014 | Smith et al. |
| 8,631,993 B2 | 1/2014 | Kostrzewski |
| 8,632,463 B2 | 1/2014 | Drinan et al. |
| 8,636,187 B2 | 1/2014 | Hueil et al. |
| 8,636,766 B2 | 1/2014 | Milliman et al. |
| 8,640,940 B2 | 2/2014 | Ohdaira |
| 8,647,258 B2 | 2/2014 | Aranyi et al. |
| 8,652,121 B2 | 2/2014 | Quick et al. |
| 8,657,174 B2 | 2/2014 | Yates et al. |
| 8,657,177 B2 | 2/2014 | Scirica et al. |
| 8,662,370 B2 | 3/2014 | Takei |
| 8,663,258 B2 | 3/2014 | Bettuchi et al. |
| 8,672,206 B2 | 3/2014 | Aranyi et al. |
| 8,672,931 B2 | 3/2014 | Goldboss et al. |
| 8,678,264 B2 | 3/2014 | Racenet et al. |
| 8,684,248 B2 | 4/2014 | Milliman |
| 8,684,250 B2 | 4/2014 | Bettuchi et al. |
| 8,684,251 B2 | 4/2014 | Rebuffat et al. |
| 8,684,252 B2 | 4/2014 | Patel et al. |
| 8,696,552 B2 | 4/2014 | Whitman |
| 8,708,213 B2 | 4/2014 | Shelton, IV et al. |
| 8,715,306 B2 | 5/2014 | Faller et al. |
| 8,733,611 B2 | 5/2014 | Milliman |
| 8,758,391 B2 | 6/2014 | Swayze et al. |
| 8,806,973 B2 | 8/2014 | Ross et al. |
| 8,808,311 B2 | 8/2014 | Heinrich et al. |
| 8,820,605 B2 | 9/2014 | Shelton, IV |
| 8,851,355 B2 | 10/2014 | Aranyi et al. |
| 8,858,571 B2 | 10/2014 | Shelton, IV et al. |
| 8,875,972 B2 | 11/2014 | Weisenburgh, II et al. |
| 8,888,762 B2 | 11/2014 | Whitman |
| 8,893,946 B2 | 11/2014 | Boudreaux et al. |
| 8,899,462 B2 | 12/2014 | Kostrzewski et al. |
| 8,905,289 B2 | 12/2014 | Patel et al. |
| 8,919,630 B2 | 12/2014 | Milliman |
| 8,931,680 B2 | 1/2015 | Milliman |
| 8,939,344 B2 | 1/2015 | Olson et al. |
| 8,950,646 B2 | 2/2015 | Viola |
| 8,960,519 B2 | 2/2015 | Whitman et al. |
| 8,961,396 B2 | 2/2015 | Azarbarzin et al. |
| 8,967,443 B2 | 3/2015 | McCuen |
| 8,968,276 B2 | 3/2015 | Zemlok et al. |
| 8,968,337 B2 | 3/2015 | Whitfield et al. |
| 8,992,422 B2 | 3/2015 | Spivey et al. |
| 9,016,545 B2 | 4/2015 | Aranyi et al. |
| 9,023,014 B2 | 5/2015 | Chowaniec et al. |
| 9,033,868 B2 | 5/2015 | Whitman et al. |
| 9,055,943 B2 | 6/2015 | Zemlok et al. |
| 9,064,653 B2 | 6/2015 | Prest et al. |
| 9,072,515 B2 | 7/2015 | Hall et al. |
| 9,113,847 B2 | 8/2015 | Whitman et al. |
| 9,113,875 B2 | 8/2015 | Viola et al. |
| 9,113,876 B2 | 8/2015 | Zemlok et al. |
| 9,113,899 B2 | 8/2015 | Garrison et al. |
| 9,216,013 B2 | 12/2015 | Scirica et al. |
| 9,241,712 B2 | 1/2016 | Zemlok et al. |
| 9,282,961 B2 | 3/2016 | Whitman et al. |
| 9,282,963 B2 | 3/2016 | Bryant |
| 9,295,522 B2 | 3/2016 | Kostrzewski |
| 9,307,986 B2 | 4/2016 | Hall et al. |
| 10,973,544 B2 * | 4/2021 | Williams ............ A61B 17/1155 |
| 2001/0031975 A1 | 10/2001 | Whitman et al. |
| 2002/0049454 A1 | 4/2002 | Whitman et al. |
| 2002/0165541 A1 | 11/2002 | Whitman |
| 2003/0038938 A1 | 2/2003 | Jung et al. |
| 2003/0111507 A1 | 6/2003 | Nunez |
| 2003/0165794 A1 | 9/2003 | Matoba |
| 2004/0034369 A1 | 2/2004 | Sauer et al. |
| 2004/0111012 A1 | 6/2004 | Whitman |
| 2004/0133189 A1 | 7/2004 | Sakurai |
| 2004/0153124 A1 | 8/2004 | Whitman |
| 2004/0176751 A1 | 9/2004 | Weitzner et al. |
| 2004/0193146 A1 | 9/2004 | Lee et al. |
| 2005/0051597 A1 | 3/2005 | Toledano |
| 2005/0107813 A1 | 5/2005 | Gilete Garcia |
| 2005/0125027 A1 | 6/2005 | Knodel et al. |
| 2005/0131442 A1 | 6/2005 | Yachia et al. |
| 2006/0000869 A1 | 1/2006 | Fontayne |
| 2006/0011698 A1 | 1/2006 | Okada et al. |
| 2006/0142656 A1 | 6/2006 | Malackowski et al. |
| 2006/0142740 A1 | 6/2006 | Sherman et al. |
| 2006/0142744 A1 | 6/2006 | Boutoussov |
| 2006/0201989 A1 | 9/2006 | Ojeda |
| 2006/0259073 A1 | 11/2006 | Miyamoto et al. |
| 2006/0278680 A1 | 12/2006 | Viola et al. |
| 2006/0284730 A1 | 12/2006 | Schmid et al. |
| 2007/0023476 A1 | 2/2007 | Whitman et al. |
| 2007/0023477 A1 | 2/2007 | Whitman et al. |
| 2007/0027469 A1 | 2/2007 | Smith et al. |
| 2007/0027473 A1 | 2/2007 | Vresh et al. |
| 2007/0029363 A1 | 2/2007 | Popov |
| 2007/0060952 A1 | 3/2007 | Roby et al. |
| 2007/0084897 A1 | 4/2007 | Shelton et al. |
| 2007/0102472 A1 | 5/2007 | Shelton |
| 2007/0152014 A1 | 7/2007 | Gillum et al. |
| 2007/0175947 A1 | 8/2007 | Ortiz et al. |
| 2007/0175949 A1 | 8/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0270784 A1 | 11/2007 | Smith et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0058801 A1 | 3/2008 | Taylor et al. |
| 2008/0109012 A1 | 5/2008 | Falco et al. |
| 2008/0110958 A1 | 5/2008 | McKenna et al. |
| 2008/0147089 A1 | 6/2008 | Loh et al. |
| 2008/0167736 A1 | 7/2008 | Swayze et al. |
| 2008/0185419 A1 | 8/2008 | Smith et al. |
| 2008/0188841 A1 | 8/2008 | Tomasello et al. |
| 2008/0197167 A1 | 8/2008 | Viola et al. |
| 2008/0208195 A1 | 8/2008 | Shores et al. |
| 2008/0237296 A1 | 10/2008 | Boudreaux et al. |
| 2008/0251561 A1 | 10/2008 | Eades et al. |
| 2008/0255413 A1 | 10/2008 | Zemlok et al. |
| 2008/0255607 A1 | 10/2008 | Zemlok |
| 2008/0262654 A1 | 10/2008 | Omori et al. |
| 2008/0308603 A1 | 12/2008 | Shelton et al. |
| 2009/0012533 A1 | 1/2009 | Barbagli et al. |
| 2009/0090763 A1 | 4/2009 | Zemlok et al. |
| 2009/0099876 A1 | 4/2009 | Whitman |
| 2009/0138006 A1 | 5/2009 | Bales et al. |
| 2009/0171147 A1 | 7/2009 | Lee et al. |
| 2009/0182193 A1 | 7/2009 | Whitman et al. |
| 2009/0209946 A1 | 8/2009 | Swayze et al. |
| 2009/0209990 A1 | 8/2009 | Yates et al. |
| 2009/0236392 A1 | 9/2009 | Cole et al. |
| 2009/0236398 A1 | 9/2009 | Cole et al. |
| 2009/0236401 A1 | 9/2009 | Cole et al. |
| 2009/0254094 A1 | 10/2009 | Knapp et al. |
| 2009/0299141 A1 | 12/2009 | Downey et al. |
| 2010/0019016 A1 | 1/2010 | Edoga et al. |
| 2010/0023022 A1 | 1/2010 | Zeiner et al. |
| 2010/0051668 A1 | 3/2010 | Milliman et al. |

(56) References Cited

U.S. PATENT DOCUMENTS

| | | |
|---|---|---|
| 2010/0069942 A1 | 3/2010 | Shelton, IV |
| 2010/0084453 A1 | 4/2010 | Hu |
| 2010/0147923 A1 | 6/2010 | D'Agostino et al. |
| 2010/0163598 A1 | 7/2010 | Belzer |
| 2010/0193568 A1 | 8/2010 | Scheib et al. |
| 2010/0211053 A1 | 8/2010 | Ross et al. |
| 2010/0224668 A1 | 9/2010 | Fontayne et al. |
| 2010/0225073 A1 | 9/2010 | Porter et al. |
| 2010/0230465 A1 | 9/2010 | Smith et al. |
| 2010/0258611 A1 | 10/2010 | Smith et al. |
| 2010/0264195 A1 | 10/2010 | Bettuchi |
| 2010/0327041 A1 | 12/2010 | Milliman et al. |
| 2011/0011916 A1 | 1/2011 | Levine |
| 2011/0071508 A1 | 3/2011 | Duval et al. |
| 2011/0077673 A1 | 3/2011 | Grubac et al. |
| 2011/0114697 A1 | 5/2011 | Baxter, III et al. |
| 2011/0114700 A1 | 5/2011 | Baxter, III et al. |
| 2011/0121049 A1 | 5/2011 | Malinouskas et al. |
| 2011/0125138 A1 | 5/2011 | Malinouskas et al. |
| 2011/0139851 A1 | 6/2011 | McCuen |
| 2011/0144640 A1 | 6/2011 | Heinrich et al. |
| 2011/0147432 A1 | 6/2011 | Heinrich et al. |
| 2011/0155783 A1 | 6/2011 | Rajappa et al. |
| 2011/0155786 A1 | 6/2011 | Shelton, IV |
| 2011/0172648 A1 | 7/2011 | Jeong |
| 2011/0174009 A1 | 7/2011 | Iizuka et al. |
| 2011/0174099 A1 | 7/2011 | Ross et al. |
| 2011/0184245 A1 | 7/2011 | Xia et al. |
| 2011/0192882 A1 | 8/2011 | Hess et al. |
| 2011/0204119 A1 | 8/2011 | McCuen |
| 2011/0218522 A1 | 9/2011 | Whitman |
| 2011/0276057 A1 | 11/2011 | Conlon et al. |
| 2011/0290854 A1 | 12/2011 | Timm et al. |
| 2011/0295242 A1 | 12/2011 | Spivey et al. |
| 2011/0295269 A1 | 12/2011 | Swensgard et al. |
| 2012/0000962 A1 | 1/2012 | Racenet et al. |
| 2012/0074199 A1 | 3/2012 | Olson et al. |
| 2012/0089131 A1 | 4/2012 | Zemlok et al. |
| 2012/0104071 A1 | 5/2012 | Bryant |
| 2012/0116368 A1 | 5/2012 | Viola |
| 2012/0143002 A1 | 6/2012 | Aranyi et al. |
| 2012/0145755 A1 | 6/2012 | Kahn |
| 2012/0172924 A1 | 7/2012 | Allen, IV |
| 2012/0193395 A1 | 8/2012 | Pastorelli et al. |
| 2012/0193398 A1 | 8/2012 | Williams et al. |
| 2012/0211542 A1 | 8/2012 | Racenet |
| 2012/0223121 A1 | 9/2012 | Viola et al. |
| 2012/0232339 A1 | 9/2012 | Csiky |
| 2012/0245428 A1 | 9/2012 | Smith et al. |
| 2012/0253329 A1 | 10/2012 | Zemlok et al. |
| 2012/0273548 A1 | 11/2012 | Ma et al. |
| 2012/0310220 A1 | 12/2012 | Malkowski et al. |
| 2012/0323226 A1 | 12/2012 | Chowaniec et al. |
| 2012/0325888 A1 | 12/2012 | Qiao et al. |
| 2012/0330285 A1 | 12/2012 | Hartoumbekis et al. |
| 2013/0015232 A1 | 1/2013 | Smith et al. |
| 2013/0018361 A1 | 1/2013 | Bryant |
| 2013/0020372 A1 | 1/2013 | Jankowski et al. |
| 2013/0020373 A1 | 1/2013 | Smith et al. |
| 2013/0032628 A1 | 2/2013 | Li et al. |
| 2013/0056516 A1 | 3/2013 | Viola |
| 2013/0060258 A1 | 3/2013 | Giacomantonio |
| 2013/0093149 A1 | 4/2013 | Saur et al. |
| 2013/0105544 A1 | 5/2013 | Mozdzierz et al. |
| 2013/0105546 A1 | 5/2013 | Milliman et al. |
| 2013/0105551 A1 | 5/2013 | Zingman |
| 2013/0126580 A1 | 5/2013 | Smith et al. |
| 2013/0153630 A1 | 6/2013 | Miller et al. |
| 2013/0153631 A1 | 6/2013 | Vasudevan et al. |
| 2013/0153633 A1 | 6/2013 | Casasanta, Jr. et al. |
| 2013/0153634 A1 | 6/2013 | Carter et al. |
| 2013/0153638 A1 | 6/2013 | Carter et al. |
| 2013/0153639 A1 | 6/2013 | Hodgkinson et al. |
| 2013/0175315 A1 | 7/2013 | Milliman |
| 2013/0175318 A1 | 7/2013 | Felder et al. |
| 2013/0175319 A1 | 7/2013 | Felder et al. |
| 2013/0175320 A1 | 7/2013 | Mandakolathur Vasudevan et al. |
| 2013/0181035 A1 | 7/2013 | Milliman |
| 2013/0181036 A1 | 7/2013 | Olson et al. |
| 2013/0184704 A1 | 7/2013 | Beardsley et al. |
| 2013/0186930 A1 | 7/2013 | Wenchell et al. |
| 2013/0193185 A1 | 8/2013 | Patel |
| 2013/0193187 A1 | 8/2013 | Milliman |
| 2013/0193190 A1 | 8/2013 | Carter et al. |
| 2013/0193191 A1 | 8/2013 | Stevenson et al. |
| 2013/0193192 A1 | 8/2013 | Casasanta, Jr. et al. |
| 2013/0200131 A1 | 8/2013 | Racenet et al. |
| 2013/0206816 A1 | 8/2013 | Penna |
| 2013/0214025 A1 | 8/2013 | Zemlok et al. |
| 2013/0214027 A1 | 8/2013 | Hessler et al. |
| 2013/0214028 A1 | 8/2013 | Patel et al. |
| 2013/0228609 A1 | 9/2013 | Kostrzewski |
| 2013/0240597 A1 | 9/2013 | Milliman et al. |
| 2013/0240600 A1 | 9/2013 | Bettuchi |
| 2013/0248581 A1 | 9/2013 | Smith et al. |
| 2013/0274722 A1 | 10/2013 | Kostrzewski et al. |
| 2013/0277411 A1 | 10/2013 | Hodgkinson et al. |
| 2013/0277412 A1 | 10/2013 | Gresham et al. |
| 2013/0282052 A1 | 10/2013 | Aranyi et al. |
| 2013/0284792 A1 | 10/2013 | Ma |
| 2013/0292449 A1 | 11/2013 | Bettuchi et al. |
| 2013/0292451 A1 | 11/2013 | Viola et al. |
| 2013/0299553 A1 | 11/2013 | Mozdzierz |
| 2013/0299554 A1 | 11/2013 | Mozdzierz |
| 2013/0306701 A1 | 11/2013 | Olson |
| 2013/0306707 A1 | 11/2013 | Viola et al. |
| 2013/0313304 A1 | 11/2013 | Shelton, IV et al. |
| 2013/0317486 A1 | 11/2013 | Nicholas et al. |
| 2013/0319706 A1 | 12/2013 | Nicholas et al. |
| 2013/0324978 A1 | 12/2013 | Nicholas et al. |
| 2013/0324979 A1 | 12/2013 | Nicholas et al. |
| 2013/0334281 A1 | 12/2013 | Williams |
| 2014/0008413 A1 | 1/2014 | Williams |
| 2014/0012236 A1 | 1/2014 | Williams et al. |
| 2014/0012237 A1 | 1/2014 | Pribanic et al. |
| 2014/0012289 A1 | 1/2014 | Snow et al. |
| 2014/0012317 A1 | 1/2014 | Orban et al. |
| 2014/0025046 A1 | 1/2014 | Williams et al. |
| 2014/0110455 A1 | 4/2014 | Ingmanson et al. |
| 2014/0166728 A1 | 6/2014 | Swayze et al. |
| 2014/0207125 A1 | 7/2014 | Applegate et al. |
| 2014/0207182 A1 | 7/2014 | Zergiebel et al. |
| 2014/0207185 A1 | 7/2014 | Goble et al. |
| 2014/0236173 A1 | 8/2014 | Sclrica et al. |
| 2014/0236174 A1 | 8/2014 | Williams et al. |
| 2014/0276932 A1 | 9/2014 | Williams et al. |
| 2014/0299647 A1 | 10/2014 | Sclrica et al. |
| 2014/0303668 A1 | 10/2014 | Nicholas et al. |
| 2014/0358129 A1 | 12/2014 | Zergiebel et al. |
| 2014/0361068 A1 | 12/2014 | Aranyi et al. |
| 2014/0365235 A1 | 12/2014 | DeBoer et al. |
| 2014/0373652 A1 | 12/2014 | Zergiebel et al. |
| 2015/0014392 A1 | 1/2015 | Williams et al. |
| 2015/0048144 A1 | 2/2015 | Whitman |
| 2015/0076205 A1 | 3/2015 | Zergiebel |
| 2015/0080912 A1 | 3/2015 | Sapre |
| 2015/0112381 A1 | 4/2015 | Richard |
| 2015/0122870 A1 | 5/2015 | Zemlok et al. |
| 2015/0133224 A1 | 5/2015 | Whitman et al. |
| 2015/0133957 A1 | 5/2015 | Kostrzewski |
| 2015/0150547 A1 | 6/2015 | Ingmanson et al. |
| 2015/0150574 A1 | 6/2015 | Richard et al. |
| 2015/0157320 A1 | 6/2015 | Zergiebel et al. |
| 2015/0157321 A1 | 6/2015 | Zergiebel et al. |
| 2015/0164502 A1 | 6/2015 | Richard et al. |
| 2015/0201931 A1 | 7/2015 | Zergiebel et al. |
| 2015/0272577 A1 | 10/2015 | Zemlok et al. |
| 2015/0297199 A1 | 10/2015 | Nicholas et al. |
| 2015/0303996 A1 | 10/2015 | Calderoni |
| 2015/0320420 A1 | 11/2015 | Penna et al. |
| 2015/0327850 A1 | 11/2015 | Kostrzewski |
| 2015/0342601 A1 | 12/2015 | Williams et al. |
| 2015/0342603 A1 | 12/2015 | Zergiebel et al. |
| 2015/0374366 A1 | 12/2015 | Zergiebel et al. |

(56) References Cited

U.S. PATENT DOCUMENTS

| | | | |
|---|---|---|---|
| 2015/0374370 A1 | 12/2015 | Zergiebel et al. | |
| 2015/0374371 A1 | 12/2015 | Richard et al. | |
| 2015/0374372 A1 | 12/2015 | Zergiebel et al. | |
| 2015/0374449 A1 | 12/2015 | Chowaniec et al. | |
| 2015/0380187 A1 | 12/2015 | Zergiebel et al. | |
| 2016/0095585 A1 | 4/2016 | Zergiebel et al. | |
| 2016/0095596 A1 | 4/2016 | Scirica et al. | |
| 2016/0106406 A1 | 4/2016 | Cabrera et al. | |
| 2016/0113648 A1 | 4/2016 | Zergiebel et al. | |
| 2016/0113649 A1 | 4/2016 | Zergiebel et al. | |
| 2017/0086879 A1* | 3/2017 | Williams | A61B 17/3417 |
| 2017/0196566 A1* | 7/2017 | Sgroi | A61B 17/1155 |
| 2017/0333077 A1* | 11/2017 | Williams | A61B 17/07207 |
| 2018/0280024 A1* | 10/2018 | Williams | A61B 17/068 |

FOREIGN PATENT DOCUMENTS

| | | |
|---|---|---|
| CA | 2824590 A1 | 4/2014 |
| CN | 1547454 A | 11/2004 |
| CN | 1957854 A | 5/2007 |
| CN | 101495046 A | 7/2009 |
| CN | 102247182 A | 11/2011 |
| DE | 1057729 B | 5/1959 |
| DE | 3301713 A1 | 7/1984 |
| DE | 202008009527 U1 | 10/2008 |
| DE | 102008053842 A1 | 5/2010 |
| EP | 0152382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |
| EP | 0705571 A1 | 4/1996 |
| EP | 1354560 A2 | 10/2003 |
| EP | 1563793 A1 | 8/2005 |
| EP | 1769754 A1 | 4/2007 |
| EP | 2055243 A2 | 5/2009 |
| EP | 2316345 A1 | 5/2011 |
| EP | 2333509 A1 | 6/2011 |
| EP | 2524656 A2 | 11/2012 |
| EP | 2524658 A1 | 11/2012 |
| EP | 2668910 A2 | 12/2013 |
| EP | 3078335 A1 | 10/2016 |
| ES | 2333509 A1 | 2/2010 |
| FR | 1136020 A | 5/1957 |
| FR | 1461464 A | 2/1966 |
| FR | 1588250 A | 4/1970 |
| FR | 2443239 A1 | 7/1980 |
| GB | 1185292 A | 3/1970 |
| GB | 2016991 A | 9/1979 |
| GB | 2070499 A | 9/1981 |
| JP | 08038488 | 2/1996 |
| JP | 2005125075 A | 5/2005 |
| KR | 20120022521 A | 3/2012 |
| NL | 7711347 A | 4/1979 |
| SU | 1509052 A1 | 9/1989 |
| WO | 8706448 A1 | 11/1987 |
| WO | 8900406 A1 | 1/1989 |
| WO | 9006085 A1 | 6/1990 |
| WO | 0154594 A1 | 8/2001 |
| WO | 2008107918 A1 | 9/2008 |
| WO | 2011108840 A2 | 9/2011 |
| WO | 2012/040984 A1 | 4/2012 |

OTHER PUBLICATIONS

Canadian Office Action corresponding to International Application No. CA 2640399 dated May 7, 2015.
Japanese Office Action corresponding to International Application No. JP 2011-197365 dated Mar. 23, 2015.
Japanese Office Action corresponding to International Application No. JP 2011-084092 dated May 20, 2015.
Japanese Office Action corresponding to International Application No. JP 2014-148482 dated Jun. 2, 2015.
Extended European Search Report corresponding to International Application No. EP 14 18 9358.6 dated Jul. 8, 2015.
Extended European Search Report corresponding to International Application No. EP 14 19 6148.2 dated Apr. 23, 2015.
Partial European Search Report corresponding to International Application No. EP 14 19 6704.2 dated May 11, 2015.
Australian Office Action corresponding to International Application No. AU 2010241367 dated Aug. 20, 2015.
Partial European Search Report corresponding to International Application No. EP 14 19 9783.3 dated Sep. 3, 2015.
Extended European Search Report corresponding to International Application No. EP 15 16 9962.6 dated Sep. 14, 2015.
Extended European Search Report corresponding to International Application No. EP 15 15 1076.5 dated Apr. 22, 2015.
Japanese Office Action corresponding to International Application No. JP 2011-084092 dated Jan. 14, 2016.
Extended European Search Report corresponding to International Application No. EP 12 19 7970.2 dated Jan. 28, 2016.
Chinese Office Action corresponding to International Application No. ON 201210560638.1 dated Oct. 21, 2015.
European Office Action corresponding to International Application No. EP 14 15 9056.2 dated Oct. 26, 2015.
Australian Examination Report No. 1 corresponding to International Application No. AU 2015200153 dated Dec. 11, 2015.
Australian Examination Report No. 1 corresponding to International Application No. AU 2014204542 dated Jan. 7, 2016.
Chinese Office Action corresponding to International Application No. CN 201310125449.6 dated Feb. 3, 2016.
Extended European Search Report corresponding to International Application No. EP 15 19 0245.9 dated Jan. 28, 2016.
Extended European Search Report corresponding to International Application No. EP 15 16 7793.7 dated Apr. 5, 2016.
European Office Action corresponding to International Application No. EP 14 18 4882.0 dated Apr. 25, 2016.
Extended European Search Report corresponding to International Application No. EP 14 19 6704.2 dated Sep. 24, 2015.
International Search Report and Written Opinion corresponding to Int'l Appln. No. PCT/US2015/051837, dated Dec. 21, 2015.
Extended European Search Report corresponding to International Application No. EP 14 19 7563.1 dated Aug. 5, 2015.
Partial European Search Report corresponding to International Application No. EP 15 19 0643.5 dated Feb. 26, 2016.
Extended European Search Report corresponding to International Application No. EP 15 16 6899.3 dated Feb. 3, 2016.
Extended European Search Report corresponding to International Application No. EP 14 19 9783.3 dated Dec. 22, 2015.
Extended European Search Report corresponding to International Application No. EP 15 17 3807.7 dated Nov. 24, 2015.
Extended European Search Report corresponding to International Application No. EP 15 19 0760.7 dated Apr. 1, 2016.
Extended European Search Report corresponding to International Application No. EP 15 17 3803.6 dated Nov. 24, 2015.
Extended European Search Report corresponding to International Application No. EP 15 17 3804.4 dated Nov. 24, 2015.
Extended European Search Report corresponding to International Application No. EP 15 18 8539.9 dated Feb. 17, 2016.
Extended European Search Report corresponding to International Application No. EP 15 17 3910.9 dated Nov. 13, 2015.
European Office Action corresponding to International Application No. EP 14 15 2236.7 dated Aug. 11, 2015.
Extended European Search Report corresponding to International Application No. EP 15 18 4915.5 dated Jan. 5, 2016.
Chinese Office Action corresponding to counterpart Int'l Appln. No. CN 201310369318.2 dated Jun. 28, 2016.
Chinese Office Action (with English translation), dated Jul. 4, 2016, corresponding to Chinese Patent Application No. 2015101559718; 23 total pages.
Copy of European Search Report EP 15 156 035.6 dated Aug. 10, 2016.
European Search Report corresponding to EP 15 184 915.5-1654 dated Sep. 16, 2016.
Australian Examination Report No. 1 corresponding to International Application No. AU 2013205872 dated Oct. 19, 2016.

(56) References Cited

OTHER PUBLICATIONS

Australian Examination Report from Appl. No. AU 2013205840 dated Nov. 3, 2016.

* cited by examiner

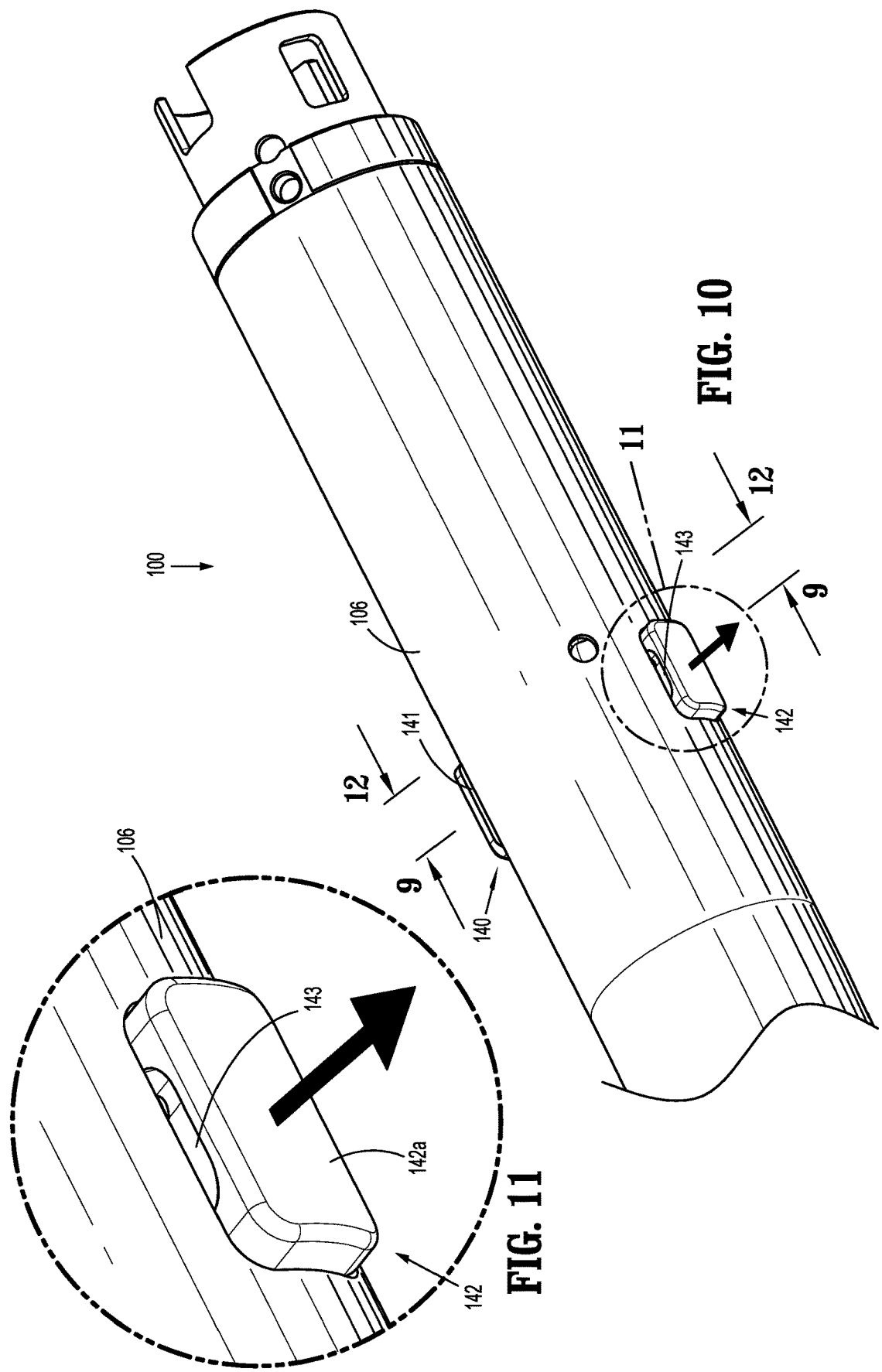

RETAINING MECHANISMS FOR TROCAR ASSEMBLIES

CROSS REFERENCE TO RELATED APPLICATIONS

The present application is a Continuation-in-Part application which claims the benefit of and priority to U.S. patent application Ser. No. 16/503,838, filed on Jul. 5, 2019, the entire content of which being incorporated by reference herein.

The present application is a Continuation-in-Part application which claims the benefit of and priority to U.S. patent application Ser. No. 16/503,726, filed on Jul. 5, 2019, the entire content of which being incorporated by reference herein.

The present application is a Continuation-in-Part application which claims the benefit of and priority to U.S. patent application Ser. No. 16/449,614, filed on Jun. 24, 2019, the entire content of which being incorporated by reference herein.

FIELD

The present disclosure relates to reusable adapter assemblies including a retaining mechanism for releasably securing a removable trocar assembly within a reusable adapter assembly. More particularly, the present disclosure relates to mechanisms for maintaining first and second button members of the retaining mechanism relative to each other during cleaning and sterilization.

BACKGROUND

Surgical devices for applying staples, clips, or other fasteners to tissue are well known. Typically, endoscopic stapling devices include an actuation unit, i.e., a handle assembly for actuating the device and a shaft for endoscopic access, and a tool assembly disposed at a distal end of the shaft. In certain of these devices, the shaft includes an adapter assembly, having a proximal end securable to the handle assembly and a distal end securable to the tool assembly.

Circular stapling devices typically include a trocar assembly for positioning an attached anvil assembly. The trocar assembly may be releasably securable within the adapter assembly to permit cleaning and sterilizing and reuse of the adapter assembly. The trocar assembly is releasably secured within the adapter assembly by a retaining mechanism.

The retaining mechanism for retaining the trocar assembly within the adapter assembly may include one or more small components that might get misplaced or lost during cleaning and sterilizing of the adapter assembly. It would be beneficial to have a retaining mechanism that includes a mechanism for maintaining the components of the retaining mechanism secured to the adapter assembly as the adapter assembly is cleaned and sterilized.

SUMMARY

An adapter assembly for connecting a loading unit to a handle assembly is provided. The adapter assembly includes an elongate body; a trocar assembly releasably securable with the elongate body, the trocar assembly including a trocar housing defining first and second openings; and a retaining mechanism configured to releasably secure the trocar assembly within the elongate body, the retaining mechanism including first and second button members configured for operable engagement by a user. The first and second button members are moveable between a lock position in which the trocar assembly is securely received with the outer sleeve and a cleanse position in which the first and second buttons extend beyond the outer sleeve. The first and second button members are secured to one another to maintain the first and second button members with the elongate body.

The first and second button members may be secured to one another with a pin and slot configuration.

The retaining mechanism may further include a first mounting member having a pin and the first button member defining a slot, wherein the pin of the first mounting member is received in the slot in the first button member.

The retaining mechanism may include a second mounting member having a pin and the second button member defining a slot, wherein the pin of the second mounting member is received in the slot in the second button.

Each of the first and second button members may include a first attachment portion and a second attachment portion. The first attachment portion of the first button member may engage the second attachment portion of the second button member, and the first attachment portion of the second button member may engage the second attachment portion of the first button member.

Each of the first and second attachment portions of each of the first and second button members may include at least one limiting feature.

The first and second button members may be secured to one another with a clip member.

The clip member may include a substantial horseshoe-shape.

The clip member may include first and second portions. The first portion may be secured to the first button member and the second portion may be secured to the second button member.

The retaining mechanism may further include a first flange extending from the first button member and a second flange extending from the second button member. The first flange may include a rivet and the second flange may define a slot. The rivet may be received in the slot to maintain the first and second button members relative to each other.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiments given below, serve to explain the principles of the disclosure, wherein:

FIG. 10 is an enlarged view of the distal portion of the adapter assembly shown in FIG. 2, with the retaining mechanism in a cleanse position;

FIG. 11 is an enlarged view of the indicated area of detail shown in FIG. 10;

DETAILED DESCRIPTION

Figure 1:
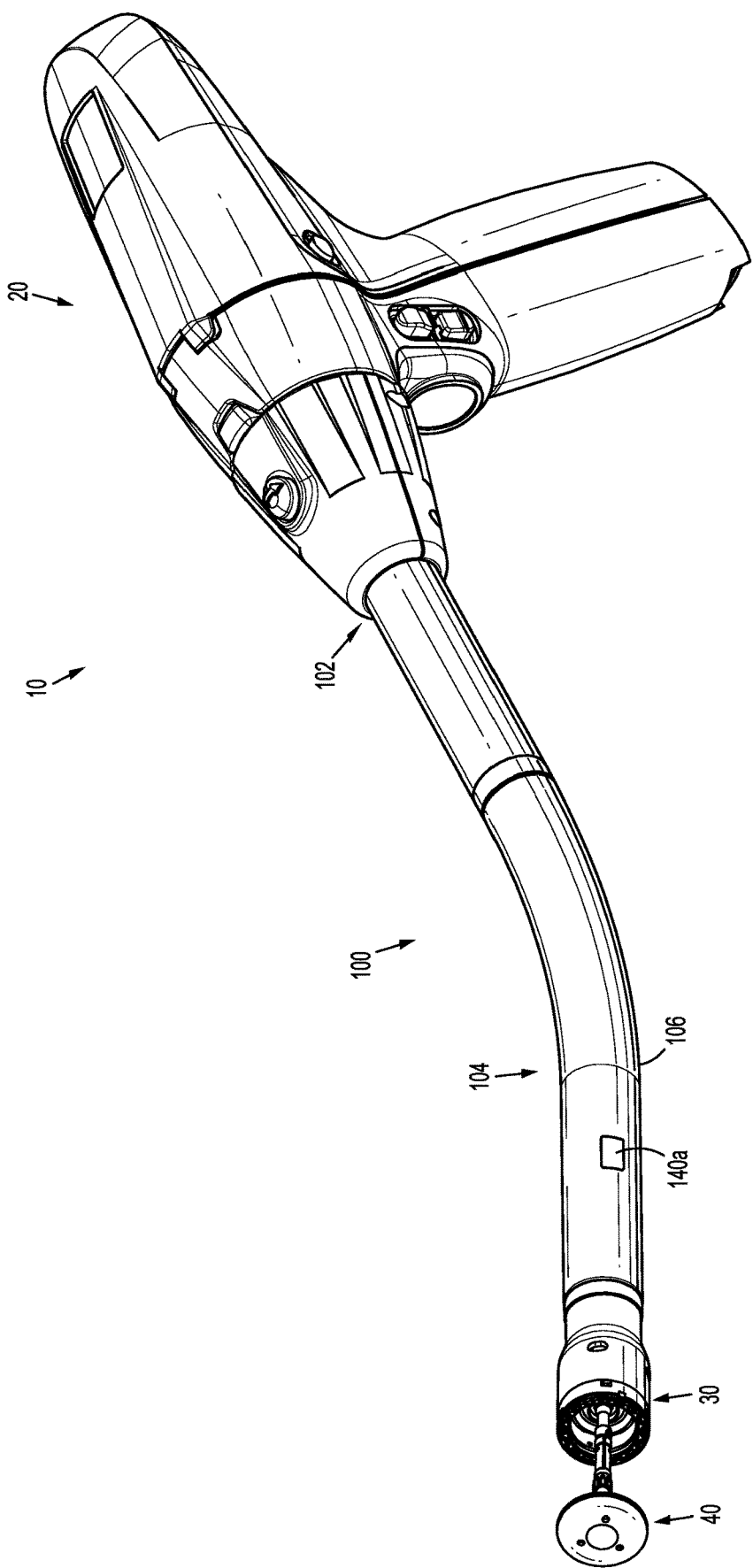
FIG. 1 is a perspective view of a surgical stapling device including a handle assembly, an adapter assembly, and a reload according to an embodiment of the present disclosure.

Embodiments of the presently disclosed adapter assembly including a retaining mechanism for securing a removable trocar assembly therein will now be described in detail with reference to the drawings in which like reference numerals designate identical or corresponding elements in each of the several views. As is common in the art, the term "proximal" refers to that part or component closer to the user or operator, i.e. surgeon or clinician, while the term "distal" refers to that part or component further away from the user.

Referring initially to FIG. 1, an adapter assembly according to an embodiment of the present disclosure, shown generally as adapter assembly 100, is a component of a surgical stapling device 10. The surgical stapling device 10 further includes a powered handle assembly 20, a loading unit 30, and an anvil assembly 40. Although shown and described with reference to surgical stapling device 10, the aspects of the present disclosure may be modified for use with manual surgical stapling devices having various configurations, and with powered surgical stapling devices having alternative configurations. For a detailed description of exemplary powered handle assemblies, please refer to commonly owned U.S. Pat. No. 9,023,014 ("the '014 patent) and U.S. Pat. Appl. Publ. No. 2012/0253329 ("the '329 application"), the content of each of which is incorporated by reference herein in their entirety.

Figure 2:
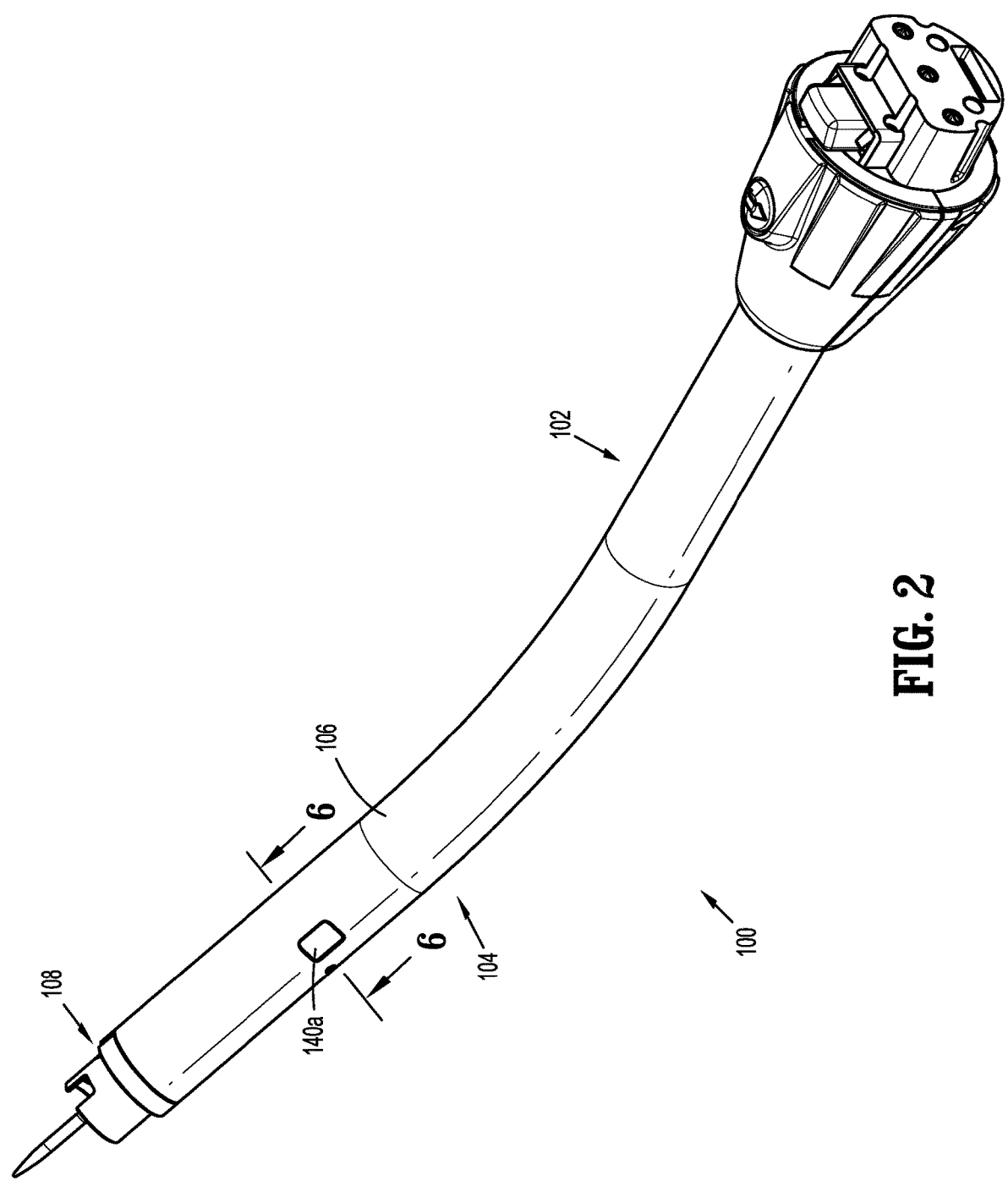
FIG. 2 is a perspective view of the adapter assembly shown in FIG. 1 with a removable trocar assembly extending from a distal portion of the adapter assembly; Shown with the reload removed exposing a tip of the removable trocar

With reference to FIG. 2, the adapter assembly 100 includes a proximal portion 102 configured for operable connection to the handle assembly 20 (FIG. 1) and a distal portion 104 configured for operable connection to the loading unit 30 (FIG. 1) and to the anvil assembly 40 (FIG. 1). Although shown and described as forming an integral unit, it is envisioned that the proximal and distal portions 102, 104 may be formed as separate units that are releasably securable to one another.

The adapter assembly 100 will only be described to the extent necessary to fully disclose the aspects of the present disclosure. For a detailed description of an exemplary adapter assembly, please refer to commonly owned U.S. Pat. App. Pub. No. 2016/0106406 ("the '406 Publication"), the content of which is incorporated by reference herein in its entirety.

Figure 3:
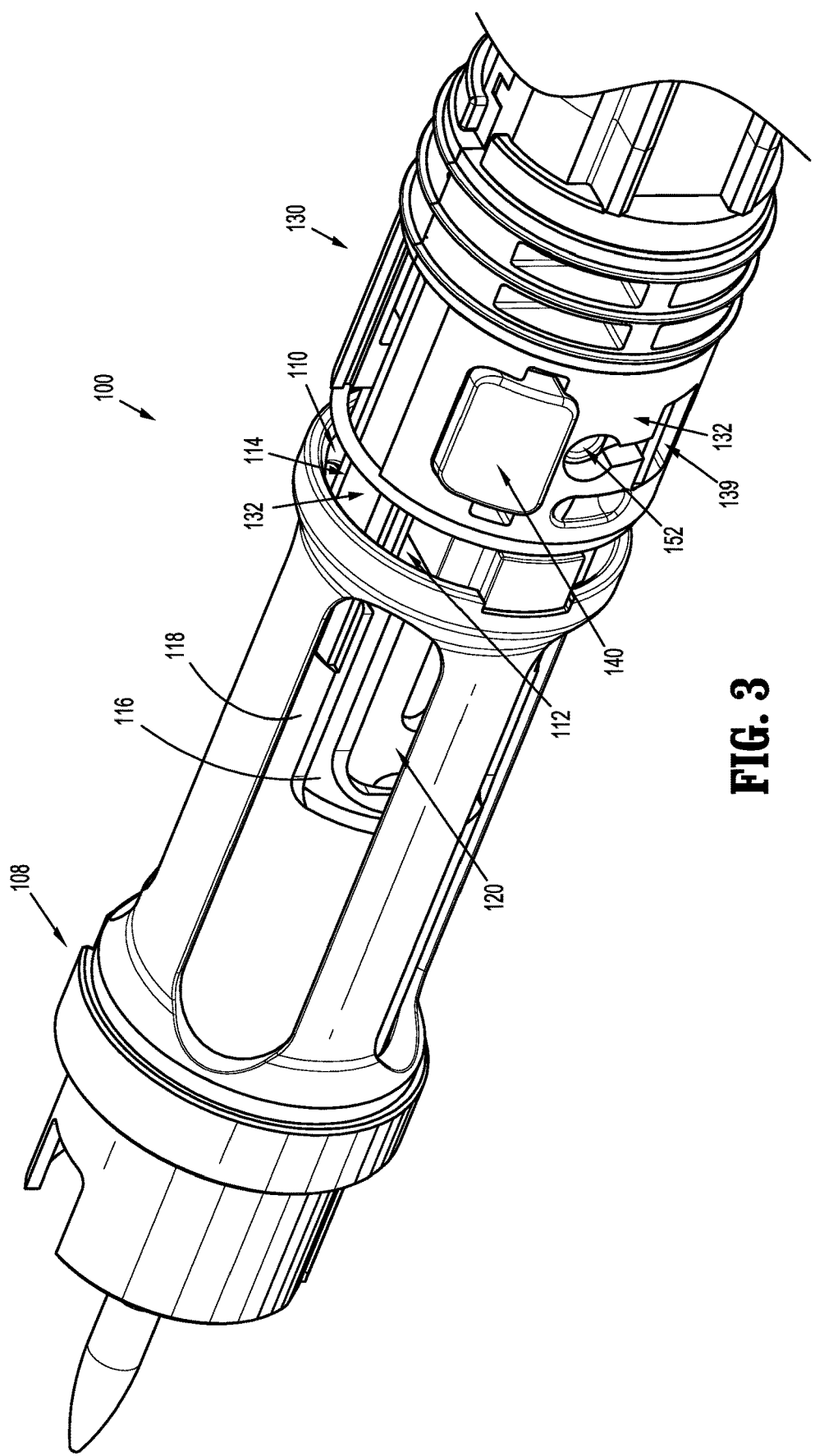
FIG. 3 is a perspective view of the distal portion of the adapter assembly with an outer sleeve removed to expose a retaining mechanism.

With additional reference to FIG. 3, the adapter assembly 100 includes an outer sleeve 106, and a connector housing 108 secured to a distal end of the outer sleeve 106. The connector housing 108 is configured to releasably secure an end effector, e.g., the end effector 30 (FIG. 1), to the adapter assembly 100.

Figure 7:
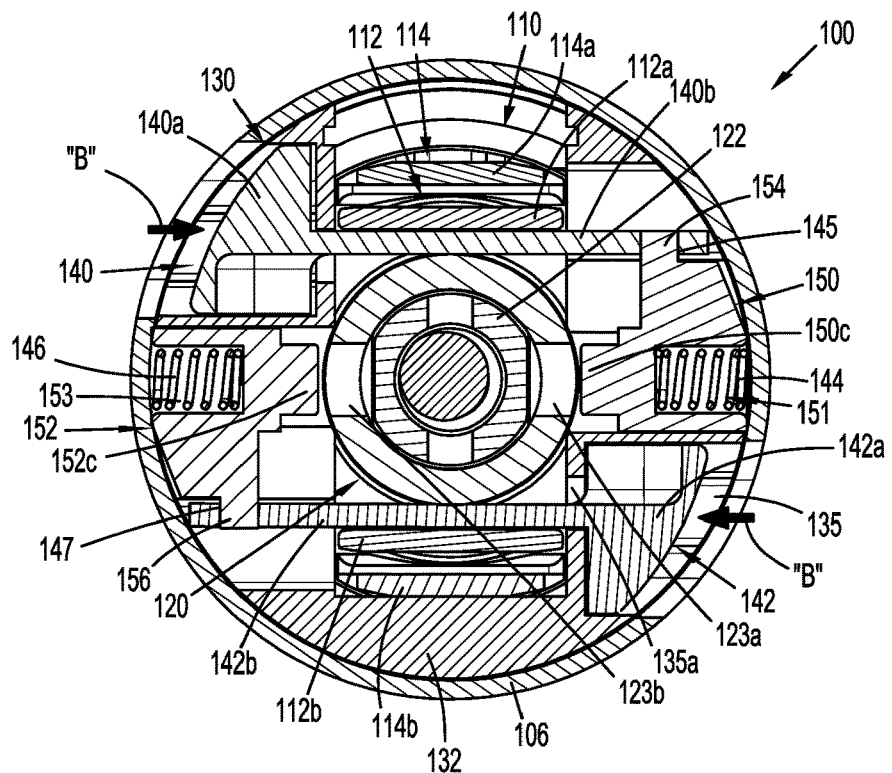
FIG. 7 is the cross-sectional end view of the adapter assembly shown in FIG. 6, with the retainer mechanism in a release position.

A drive assembly 110 (FIG. 3) extends through the outer sleeve 106 (FIG. 2) of the adapter assembly 100, and includes an inner flexible band assembly 112 and an outer flexible band assembly 114. The inner flexible band assembly 112 includes first and second flexible bands 112a, 112b (FIG. 7), and an inner pusher member 116 (FIG. 3) connected to the distal ends of the first and second flexible bands 112a, 112b (FIG. 7). Similarly, the outer flexible band assembly 114 includes first and second flexible bands 114a, 114b (FIG. 7), and an outer pusher member 118. For a detailed description of the structure and function of an exemplary drive assembly, please refer to the '406 Publication, the content of which was previously incorporated herein by reference in its entirety.

Figure 4:
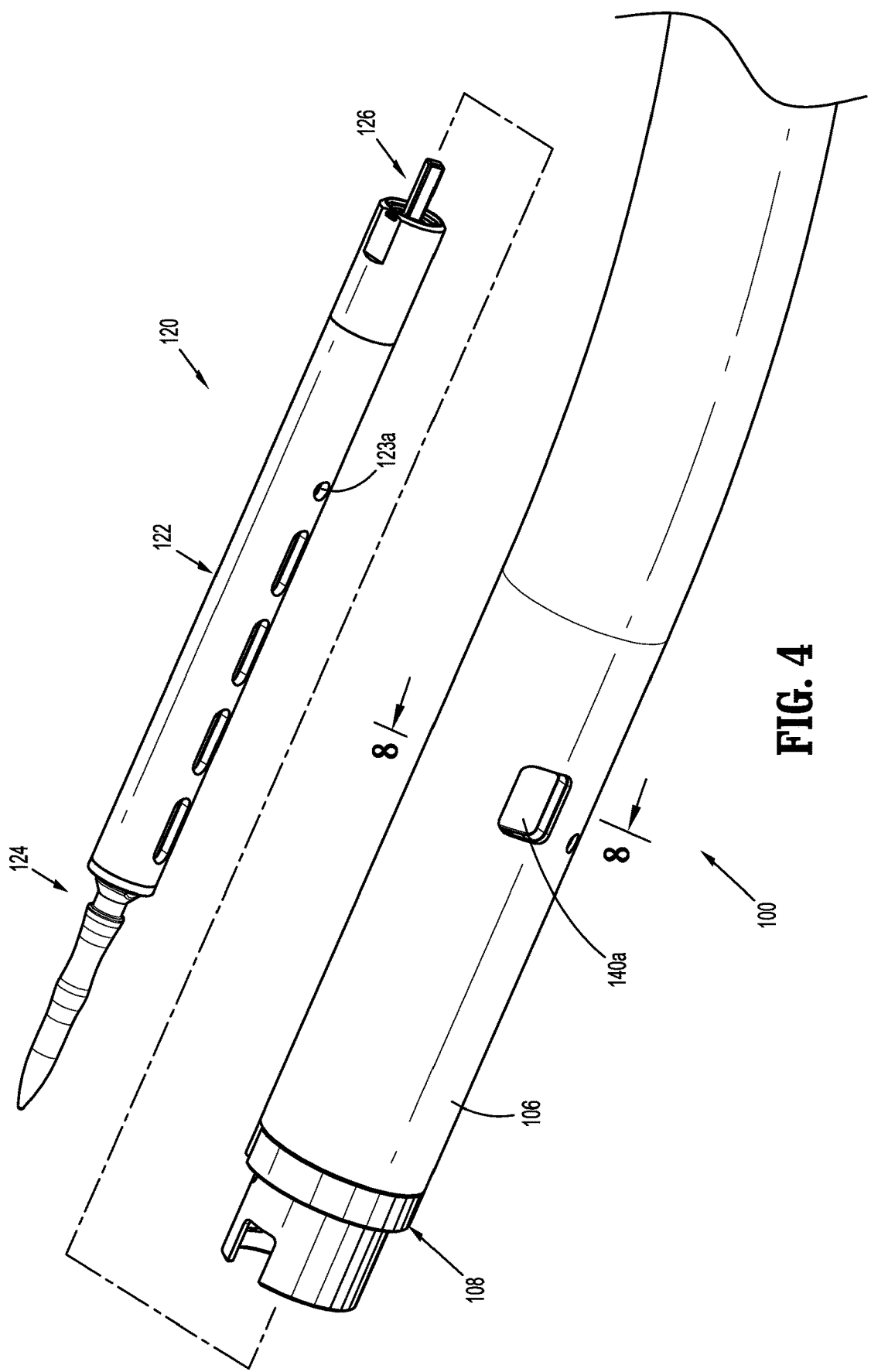
FIG. 4 is a side perspective view of the removable trocar assembly and distal portion of the adapter assembly shown in FIG. 2, with the removable trocar removed from within the adapter assembly.

With additional reference to FIG. 4, the adapter assembly 100 further includes a trocar assembly 120, and a retaining mechanism 130 (FIG. 3) releasably securing the trocar assembly 120 relative to the outer sleeve 106 (FIG. 4) of the adapter assembly 100. The trocar assembly 120 will only be described to the extent necessary to describe the aspects of the present disclosure. For a detail description of the structure and function of an exemplary trocar assembly, please refer to the '406 Publication, the content of which was previously incorporated by reference herein in its entirety.

With particular reference to FIG. 4, the trocar assembly 120 of the adapter assembly 100 (FIG. 2) includes a trocar housing 122, a trocar member 124 slidably disposed within the trocar housing 122, and a drive screw 126 operably received within the trocar member 124 for axially moving the trocar member 124 relative to the trocar housing 122. The trocar housing 122 defines first and second locking openings 123a, 123b (FIG. 7) for receiving respective flange portions 150c, 152c of first and second plunger members 150, 152 (FIG. 7) of a retaining mechanism 130 of the adapter assembly 100.

Figure 5:
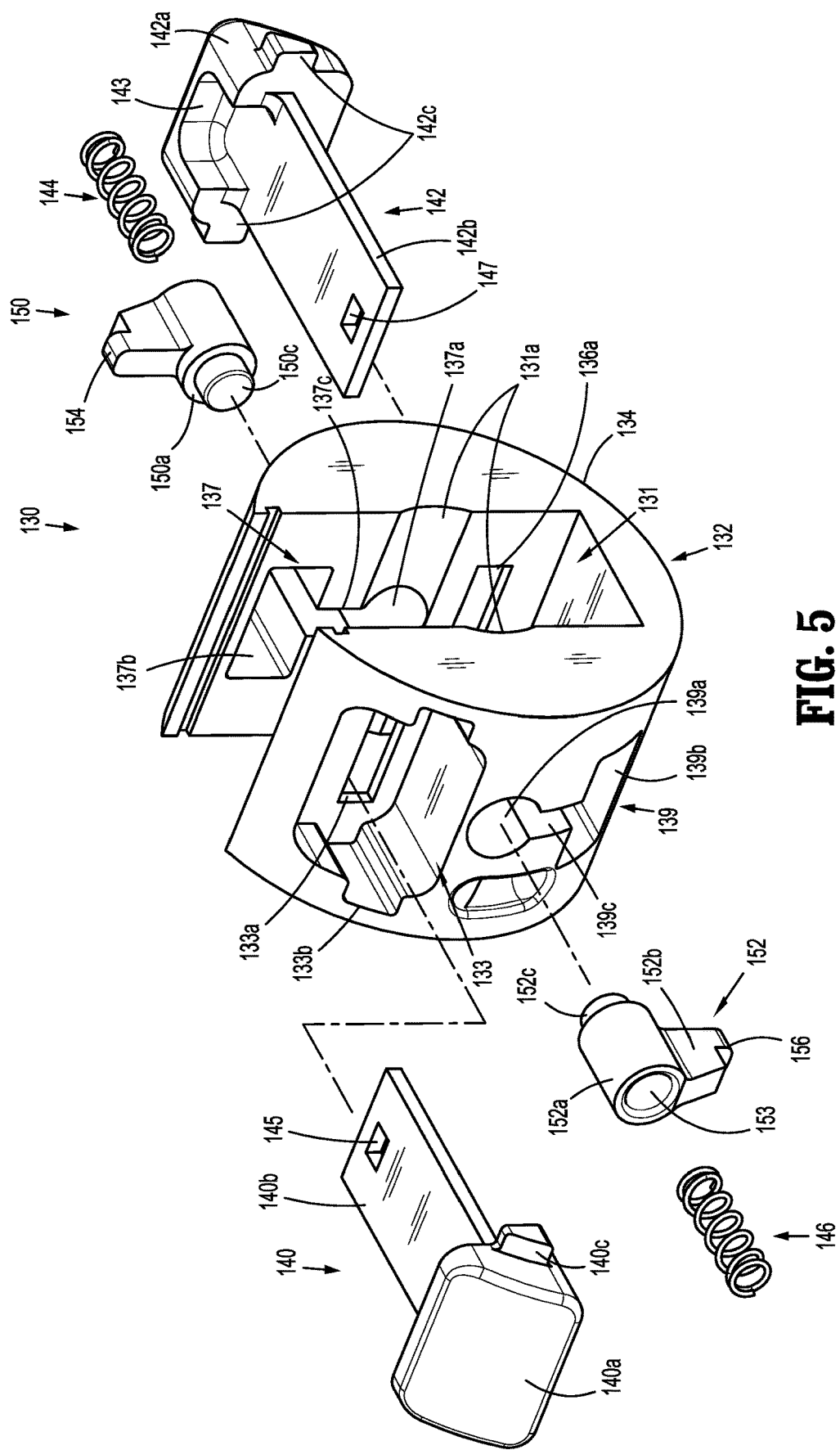
FIG. 5 is a side perspective view of the retaining mechanism shown in FIG. 3, with components separated.

With particular reference now to FIG. 5, the retaining mechanism 130 of the adapter assembly 100 (FIG. 2) includes a housing 132 supported within the outer sleeve 106 (FIG. 4) of the adapter assembly 100, first and second button members 140, 142 operably supported within the housing 132 and configured for engagement by a user, and first and second plunger members 150, 152 operably supported within the housing 132 and in engagement with the respect first and second button members 140, 142. As will be described in further detail below, first and second spring members 144, 146 are disposed within the housing 132 and bias the respective plunger members 150, 152 inward.

With continued reference to FIG. 5, the housing 132 of the retaining mechanism 130 includes a substantially cylindrical body portion 134 disposed within the outer sleeve 106 of the adapter assembly 100. The body portion 134 of the housing 132 defines a longitudinal cutout 131 for accommodating the first and second flexible bands 112*a*, 114*a*, 112*b*, 114*b* (FIG. 7) of the respective inner and outer flexible band assemblies 112, 114 of the adapter assembly 100, and for receiving the trocar assembly 120.

The body portion 134 of the housing 132 of the retaining mechanism 130 further defines first and second cutouts 133, 135 (FIG. 6) with corresponding first and second slots 133*a*, 135*a*, and corresponding first and second sets of reliefs 133*b*, 135*b*. The first and second cutouts 133, 135 operably receive respective engagement portions 140*a*, 142*a* of the first and second button member 140, 142 of the retaining mechanism 130, while the first and second slots 133*a*, 135*a* accommodate attachment portions 140*b*, 142*b* of the first and second button members 140, 142, respectively. The body portion 134 of the housing 132 further defines first and second recesses 137, 139 that accommodate the respective first and second plunger members 150, 152. The first and second recesses 137, 139 each include a cylindrical portion 137*a*, 139*b*, connected to a rectangular portion 137*b*, 139*b* by a respective channel 137*c*, 139*c*.

As noted above, the first and second button members 140, 142 of the retaining mechanism 130 each includes the engagement portion 140*a*, 142*a*, respectively, and the attachment portions 140*b*, 142*b*, respectively, extending longitudinally from the respective engagement portions 140*a*, 142*a*. The first and second button members 140, 142 further include tab portions 140*c*, 142*c*, respectively, extending laterally outwardly from the respective first and second engagement portions 140*a*, 142*a* of the respective first and second button members 140, 142.

Figure 12:
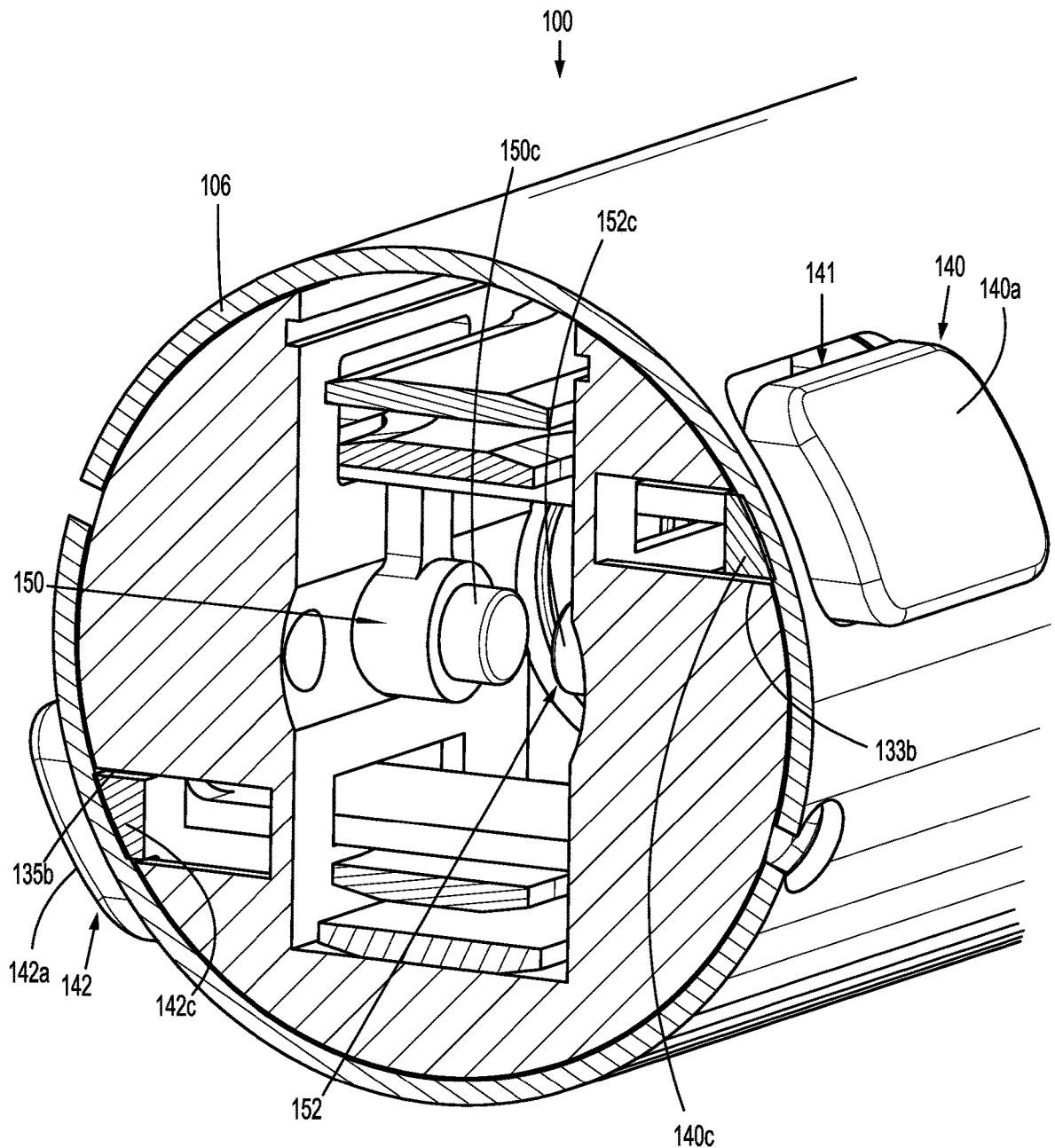
FIG. 12 is a cross-sectional end view taken along section line 12-12 shown in FIG. 10.

The engagement portions 140*a*, 142*a* of the first and second button members 140, 142 of the retaining mechanism 130 are operably received within the respective first and second cutouts 133, 135 of the housing 132 of the retaining mechanism 130 while the attachment portions 140*b*, 142*b* are slidingly received through the slots 133*a*, 135*a* (FIG. 6), respectively, corresponding to and in communication with the respective first and second cutouts 133, 135 (FIG. 12). The tab portions 140*c*, 142*c* of the respective first and second button members 140, 142 are received within the respective sets of reliefs 133*b*, 135*b* (FIG. 12) of the respective first and second cutouts 133, 135, and engage the outer sleeve 106 of the adapter assembly 100 to retain the respective first and second button members 140, 142 within the first and second cutouts 133*b*, 135*b* (FIG. 12), respectively.

The engagement portions 140*a*, 142*a* of the respective first and second button members 140, 142 of the retaining mechanism 130 each define a flush cutout 141 (FIG. 6), 143, respectively. As will be described below, the engagement portions 140*a*, 142*a* of the respective first and second button members 140, 142 extend outwardly from the outer sleeve 106 of the adapter assembly 100 when the trocar assembly 120 is removed from the adapter assembly 100 to expose the flush cutouts 141, 143 of the respective first and second button members 140, 142. The flush cutouts 141, 143 enable cleaning and sterilizing of the interior of the adapter assembly 100 without removing the retaining mechanism 130 from within the adapter assembly 100.

As noted above, the engagement portions 140*a*, 142*a* of the respective first and second button members 140, 142 of the retaining mechanism 130 are configured for operable engagement by a user. As will be detail below, engagement of the engagement portions 140*a*, 142*a* by a user to move the respective first and second button members 140, 142 inward within the first and second cutouts 133, 135, respectively, cause outward movement of the plunger members 150, 152 which permits release of the trocar assembly 120 from within the adapter assembly 100 and/or facilitates receipt of the trocar assembly 120 within adapter assembly 100.

The attachment portions 140*b*, 142*b* of the respective first and second button members 140, 142 of the retaining mechanism 130 each define an opening 145, 147 for receiving free ends 154, 156 of a flange portion 150*b*, 152*b*, respectively, of the respective first and second plunger members 150, 152. Receipt of free ends 154, 156 of the flange portions 150*b*, 152*b* of the respective first and second plunger members 150, 152 within the respective opening 145, 147 of the respective attachment portions 140*b*, 142*b* of the first and second button members 140, 142, respectively, couples the respective first and second plunger members 150, 152 to the first and second button members 140, 142, respectively, such that movement of the respective first and second button members 140, 142 causes corresponding movement of the respective first and second plunger members 150, 152.

With continued reference to FIG. 5, each of the first and second plunger members 150, 152 of the retaining mechanism 130 include a cylindrical portion 150*a*, 152*a*, respectively, the flange portion 150*b*, 152*b*, respectively, extending outwardly from the respective cylindrical portion 150*a*, 152*a*, and a locking portion 150*c*, 152*c* extending longitudinally from the cylindrical portion 150*a*, 152*a*, respectively. The first and second plunger members 150, 152 each define a recess 151, 153, respectively, for receiving at least a portion of the first and second spring members 144, 146, respectively.

The cylindrical portions 150*a*, 152*a* of the respective first and second plunger members 150, 152 of the retaining mechanism 130 are received within the respective cylindrical portions 137*a*, 139*a* of the first and second recesses 137, 139, respectively, in the housing 132 of the retaining mechanism 130. The flange portions 150*b*, 152*b* of the respective first and second plunger members 150, 152 extend through the respective channel portions 137*c*, 139*c* of the first and second recesses 137, 139, respectively, with the free ends 154, 156 of the respective flange portions 150*b*, 152*b* of the respective first and second plunger members 150, 152 received within the respective rectangular portions 137*b*, 139*b* of the first and second recesses 137, 139, respectively. The flange portion 150*b*, 152*b* of the respective first and second plunger members 150, 152 engage the respective attachment portions 140*b*, 142*b* of the respective first and second button members 140, 142, within the respective rectangular portions 137*b*, 139*b* of the first and second recesses 137, 139, respectively.

Figure 6:
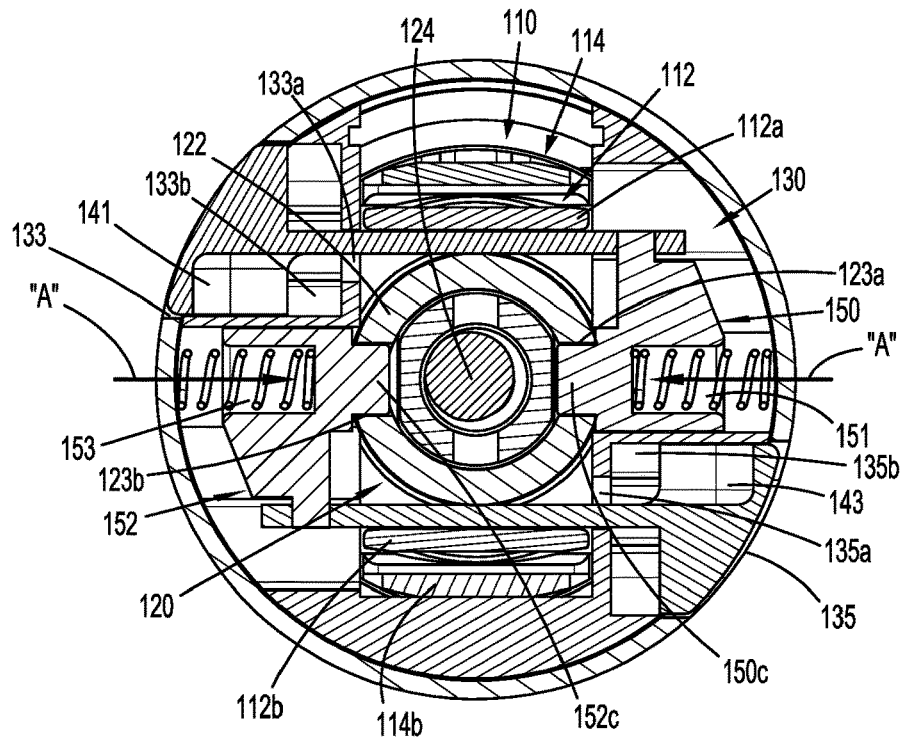
FIG. 6 is a cross-sectional end view the adapter assembly shown in FIG. 2 taken along line 6-6, with the retainer mechanism in a lock position.

The first and second spring members 144, 146 of the retaining mechanism 130 are received within the respective recesses 151, 153 in the first and second plunger members 150, 152, respectively, and bias the respective first and second plunger members 150, 152 inwardly, as indicated by arrow "A" in FIG. 6.

Although the retaining mechanism 130 is shown as including first and second button members 150, 152, and corresponding first and second plunger members 140, 142, it is envisioned that the retaining mechanism 130 may include only one button member and only one corresponding plunger member.

The first and second button members 150, 152 of the retaining mechanism 130, and the corresponding plunger members 140, 142 of the retaining mechanism 130 are movable between a first or lock position (FIG. 6), a second or release position (FIG. 7), and a third or cleanse position (FIG. 11). As will be described in further detail below, when in the lock position, the trocar assembly 120 is secured within the adapter assembly 100, while in the release position, the trocar assembly 120 may be inserted into and withdrawn from the adapter assembly 100, and in the cleanse position, the first and second button members 140, 142 extend outwardly of the sleeve 106 of the adapter assembly 100 to expose the flush ports 141, 143 of the respective first and second button members 140, 142.

With reference to FIG. 6, the first and second button members 140, 142, and the corresponding plunger members 150, 152 are shown in the lock position. In the lock position the trocar assembly 120 is fully seated within the adapter assembly 100 and is securely engaged by the retaining mechanism 130. More particularly, when in the lock position, the locking portions 150c, 152c of the respective first and second plunger members 150, 152 are received within the respective first and second openings 123a, 123b in the trocar housing 122 of the trocar assembly 120. In addition, the engagement portions 140a, 142a of the respective first and second button members 140, 142 are flush with the outer sleeve 106 of the adapter assembly 100. Maintaining the first and second button members 140, 142 flush with the outer sleeve 106 facilitates insertion of the adapter assembly 100 through an access port, lumen, and/or incision, and/or may reduce the likelihood of contaminates getting within the adapter assembly.

Figure 8:
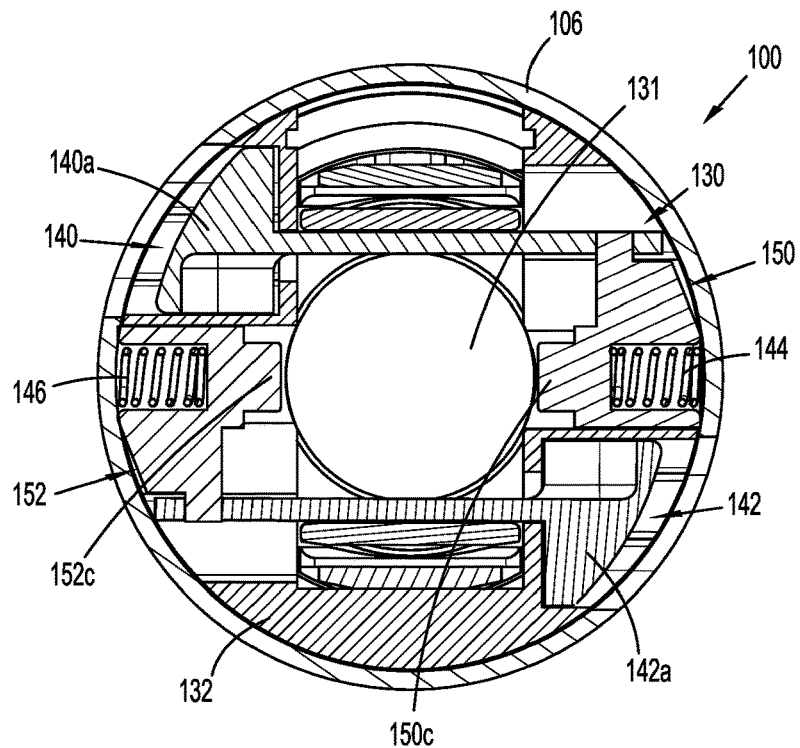
FIG. 8 is the cross-sectional end view of the adapter assembly shown in FIG. 6, with the retainer mechanism in a release position, and the trocar assembly removed.
Figure 9:
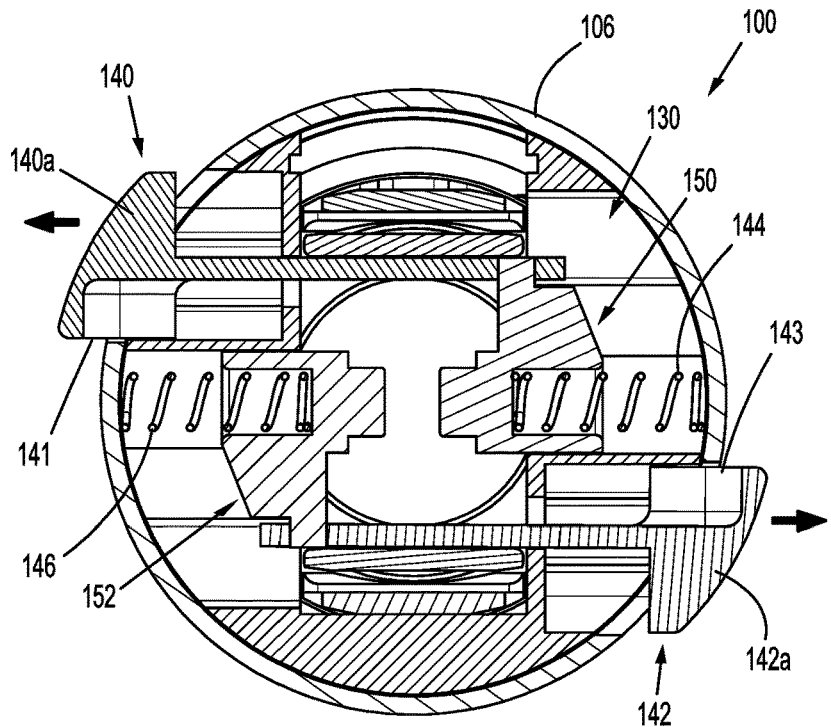
FIG. 9 is a cross-sectional end view taken along section line 9-9 shown in FIG. 10, with the retaining mechanism in a cleanse position.

Turning to FIGS. 7 and 8, the first and second button members 150, 152, and the corresponding plunger members 150, 152 are shown in the release position. In the release position, the retaining mechanism 130 (FIG. 7) is disengaged from the trocar assembly 120 so the trocar assembly 120 may be removed from within the adapter assembly 100 (FIG. 8). More particularly, the first and second button members 140, 142 of the retaining mechanism 130 are depressed, as indicated by arrows "B" in FIG. 7, to cause the respective first and second plunger members 150, 152 to move against the bias of the respective first and second spring members 144, 146, e.g., outwardly. As the first and second plunger members 150, 152 move outwardly, the flange portions 150c, 152c of the respective first and second plunger members 150, 152 withdraw from within the respective first and second openings 123a, 123b in the trocar housing 122 of the trocar assembly 120. With the first and second plunger members 150, 152 no longer engaging the trocar assembly 120, the trocar assembly 120 is removable from within the adapter assembly 100 for replacement and/or cleaning and sterilizing.

With reference now to FIGS. 9-12, the first and second button members 140, 142, and the corresponding plunger members 150, 152 of the retaining mechanism 130 are shown in the cleanse position. In the cleanse position the trocar assembly 120 is removed from the adapter assembly 100 and the first and second spring members 144, 146 bias the respective first and second plunger members 150, 152 inward. Without the trocar assembly 120 (FIG. 5) obstructing the movement of the first and second plunger members 150, 152, the first and second plunger members 150, 152 move closer together than when the first and second plunger members 150, 152 are in the lock position. In the cleanse position, the first and second button members 140, 142 are moved outwardly by the respective first and second plunger members 150, 152 beyond the outer sleeve 106 of the adapter assembly 100 by the respective first and second spring members 144, 146.

When the first and second button members 140, 142 of the retaining mechanism 130 extend beyond the outer sleeve 106 of the adapter assembly 100 the flush cutouts 141, 143 in the respective first and second button members 140, 142 are exposed to facilitate cleansing and sterilizing of the adapter assembly 100. As noted above, the tab portions 140c, 142c of the respective first and second button members 140, 142 engage an inner wall of the outer sleeve 106 of the adapter assembly 100 to maintain the respective first and second button member 140, 142 within the outer sleeve 106 of the adapter assembly 100. In this manner, the outer sleeve 106 acts as a limit stop.

The adapter assembly 100 may be provided to a clinician with the trocar assembly 120 preloaded. In the event the trocar assembly 120 is provided to the clinician separate from the adapter assembly 100, the trocar assembly 120 is loaded into the adapter assembly 100 in the reverse order of removal. In order to accommodate the trocar assembly 120 through the longitudinal passage 131 of the housing 132 of the retaining mechanism 130 the first and second button members 140, 142 are depressed, as shown in FIGS. 7 and 8, to move the first and second plunger members 150, 152, respectively, away from each other. As shown in FIG. 8, when the first and second plunger members 150, 152 are moved away from each other, the longitudinal passage 131 through the housing 132 is unobstructed, thereby allowing for receipt of the trocar assembly 120 therethrough.

Once the trocar assembly 120 is received within the adapter assembly 100, the first and second button members 140, 142 are released thereby allowing the respective first and second plunger members 150, 152 to move towards one another in response to the bias of the first and second spring members 144, 146. If the first and second openings 123a, 123b in the trocar housing 122 of the trocar assembly 120 are aligned with the flange portions 150c, 152c, respectively, of the respective first and second plunger members 150, 152 the flange portions 150c, 152c of the respective first and second plunger members 150, 152 are received within the respective first and second openings 123a, 123b and the engagement portions 140a, 142c of the respective first and second button members 140, 142 become flush with the outer sleeve 106 of the adapter assembly 100. In the event that the locking portions 150c, 152c of the respective first and second plunger members 150, 152 do not align with the respective first and second openings 123a, 123b in the trocar housing 122, the engagement portions 140a, 142a of the respective first and second button members 140, 142 remain extended beyond the outer sleeve 106, thereby indicating to the clinician that the trocar assembly is not properly seated within the adapter assembly 100.

Once the trocar assembly 120 is properly seated and secured within the adapter assembly 100, the adapter assembly 100 operates in a traditional manner.

Embodiments of retaining mechanisms that include a mechanism for securing components of the retaining mechanism to an adapter assembly during cleaning and sterilizing of the adapter assembly will be shown and described with reference to FIGS. 13-21.

Figure 13:
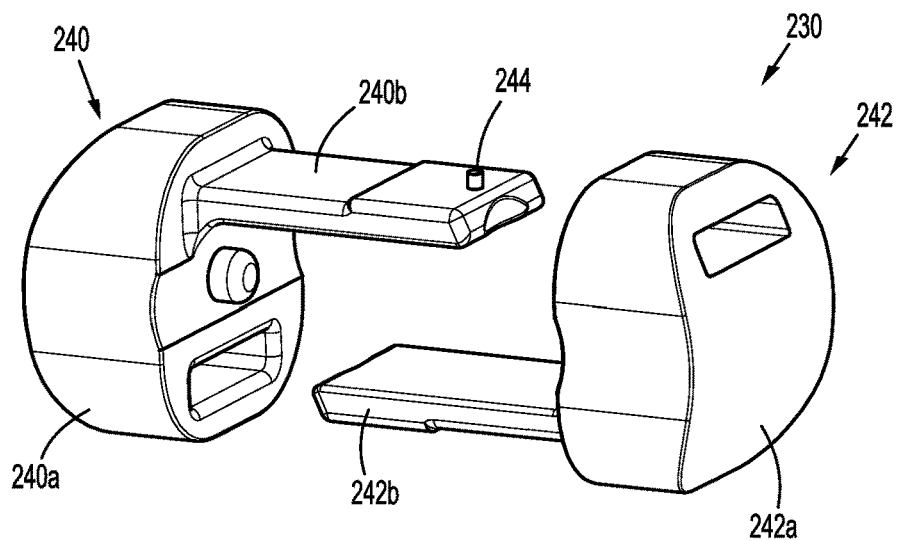
FIG. 13 is a perspective view of a retaining mechanism according to another embodiment of the present disclosure.
Figure 14:
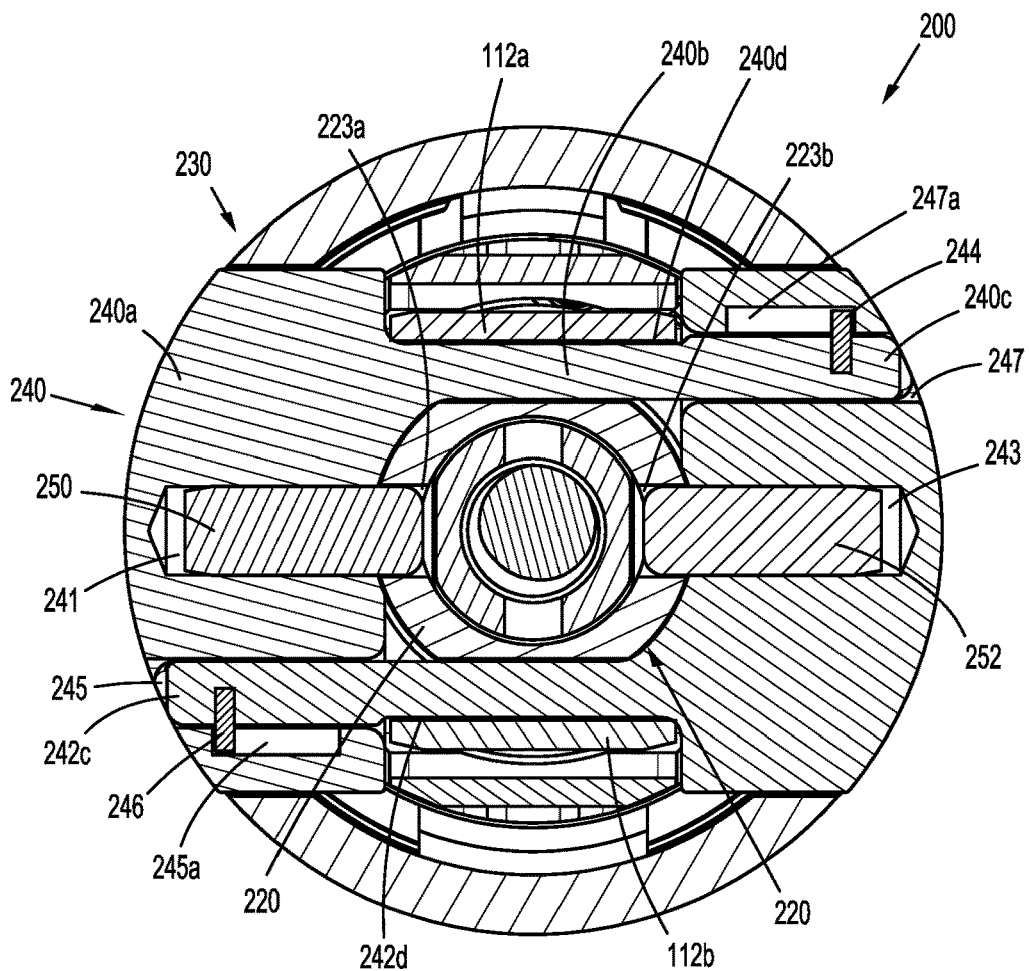
FIG. 14 is a cross-sectional end view of the retaining mechanism shown in FIG. 13 disposed within an adapter assembly and securing a trocar assembly.
Figure 15:
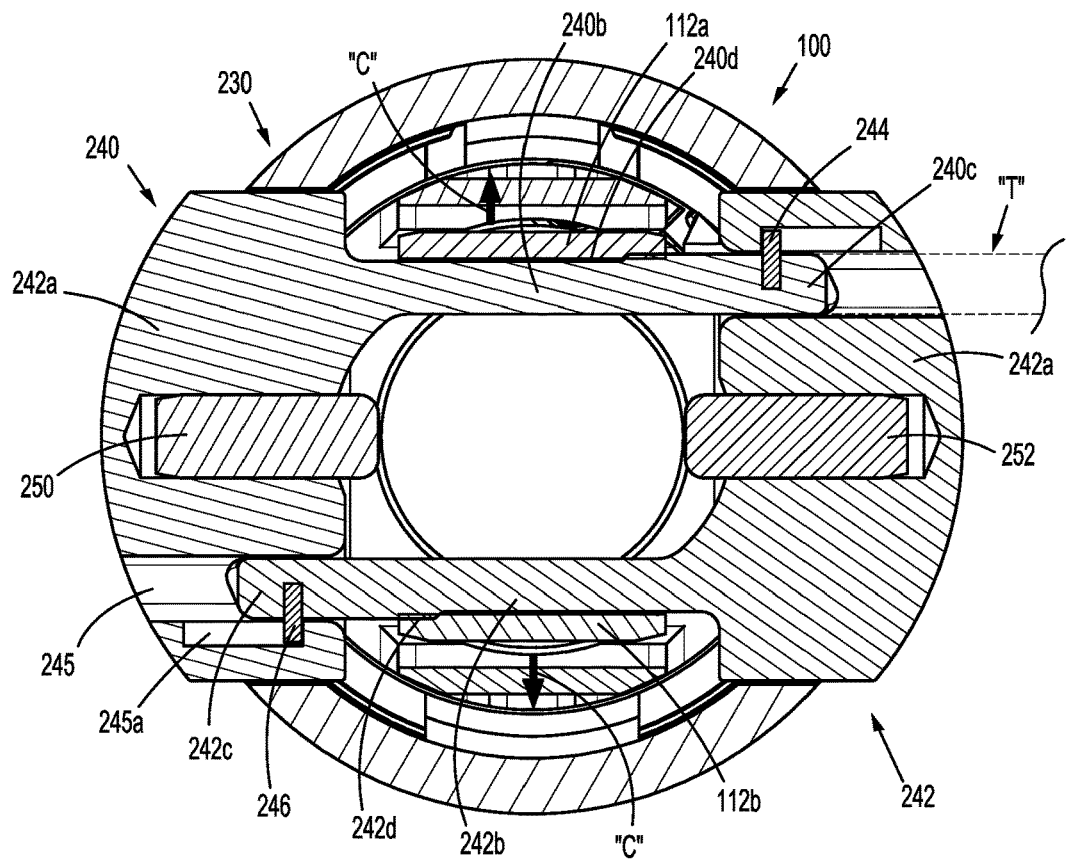
FIG. 15 is the cross-sectional end view of the retaining mechanism shown in FIG. 14, with the retaining mechanism in a release position and the trocar assembly removed.

Referring now to FIGS. 13-15, a retaining mechanism according to an embodiment of the present disclosure is shown generally as retaining mechanism 230. The retaining mechanism 230 includes first and second button members 240, 242. Each of the first and second button members 240, 242 includes an engagement portion 240a, 242a, an attachment portion 240b, 242b extending from the respective engagement portion 240a, 242a, and a pin 244, 246, respectively, disposed on a respective free end 240c, 242c of the attachment portion 240b, 242b, respectively.

Each of the first and second button members 240, 242 of the retaining mechanism 230 further defines a cavity 241, 243. First and second pegs 250, 252 are received within the respective cavity 241, 243 and extend inwardly therefrom. The first and second pegs 250, 252 are configured to be selectively received within openings 223a, 223b in a trocar housing 222 of a trocar assembly 220. Although shown as being separate components, it is envisioned that the first and second pegs 250, 252 may be integrally formed with respective first and second button members 240, 242.

The first button member 240 of the retaining mechanism 230 defines a slot 245 for slidingly receiving the attachment portion 242b of the second button member 242. The first button member 240 further defines a cutout 245a (FIG. 14) in communication with the slot 245 for receiving the pin 246 of the second button member 242. Similarly, the second button member 242 defines a slot 247 for slidingly receiving the attachment portion 240b of the first button member 240. The second button member 242 further defines a cutout 247a (FIG. 14) in communication with the slot 247 for receiving the pin 244 of the first button member 240.

With reference now to FIGS. 14 and 15, the first and second button members 240, 242 of the retaining mechanism 230 are configured to releasably engage a trocar assembly 220. More particularly, the attachment portion 240b of the first button member 240 of the retaining mechanism 230 is received within the slot 247 of the second button member 242 with the pin 244 of the first button member 240 received within the cutout 247 in the second button member 242. Similarly, the attachment portion 242b of the second button member 242 of the retaining mechanism 230 is received within the slot 245 of the first button member 240 with the pin 246 of the second button member 242 received within the cutout 245a in the first button member 240.

The first and second button members 240, 242 of the retaining mechanism 230 are moveable relative to each other between a first or lock position (FIG. 14) and a second or release position (FIG. 15). With reference to FIG. 14, when the first and second button members 240, 242 of the retaining mechanism 230 are in the lock position, the first and second pegs 250, 252 that extend from the respective first and second button members 240, 242 are received within the first and second openings 223a, 223b in the trocar housing 222 of the trocar assembly 220. Receipt of the first and second pegs 250, 252 of the retaining mechanism 230 within the first and second openings 223a, 223b of the trocar housing 222 secure the trocar assembly 220 within an adapter assembly 200.

The first and second button members 240, 242 of the retaining mechanism 230 may be maintained in the lock position by friction, mechanical fasteners (not shown), or in any other suitable manner. In embodiments, and as shown, the first and second button members 240, 242 are maintained in the first position by the respective first and second flexible bands 112a, 112b of the inner flexible band assembly 112. More particularly, each of the first and second button members 240, 242 defines a recess or cutout 240d, 242d adjacent the first and second flexible bands 112a, 112b, respectively, of the inner flexible band assembly 112. When the first and second button members 240, 242 are in the locked position, the first and second flexible bands 112a, 112b, respectively, are received within the respective recess 240d, 242d and frictional engage the respective first and second button members 240, 242 to frictionally retain the first and second button members 240, 242 in the locked position.

Turning to FIG. 15, when the first and second button members 240, 242 of the retaining mechanism 230 are in the release position, the first and second pegs 250, 252 that extend from the respective first and second button members 240, 242 are spaced from the trocar housing 222 of the trocar assembly 220 to permit removal of the trocar assembly 220 (FIG. 14) from within the adapter assembly 200.

The first and second button members 240, 242 of the retaining mechanism 230 may be moved to the release position with a tool "T". More particularly, an end of a tool "T" is inserted into one or both of the slots 245, 247 in the respective first and second button members 240, 242 such that the end of the tool "T" engages the attachment portion 242b, 240b of the respective second and first button members 242, 240. Inward force on either or both of the attachment portions 240b, 242b of the respective first and second button members 240, 242 causes the first and second button members 240, 242 causes the first and second flexible bands 112a, 112b to flex radially outward of the respective recesses 240d, 242d, as indicated by arrows "C", and to slide away from each other.

As shown in FIG. 15, the pins 244, 246 of the first and second button members 240, 242 of the retaining mechanism 230 slide within the slots 247a, 245a of the respective second and first button members 242, 240. Engagement of the pins 244, 246 of the respective first and second button members 240, 242 with the attachment portions 242b, 240b of the respective second and first button members 242, 240 limits the travel of the first and second button members 240, 242 relative to each other. In this manner, the first and second button members 240, 242 of the retaining mechanism 230 remain secured to the adapter assembly 200, thereby preventing loss of either or both of the first and second button members 240, 242 during cleaning and sterilizing of the adapter assembly 200.

Figure 16:
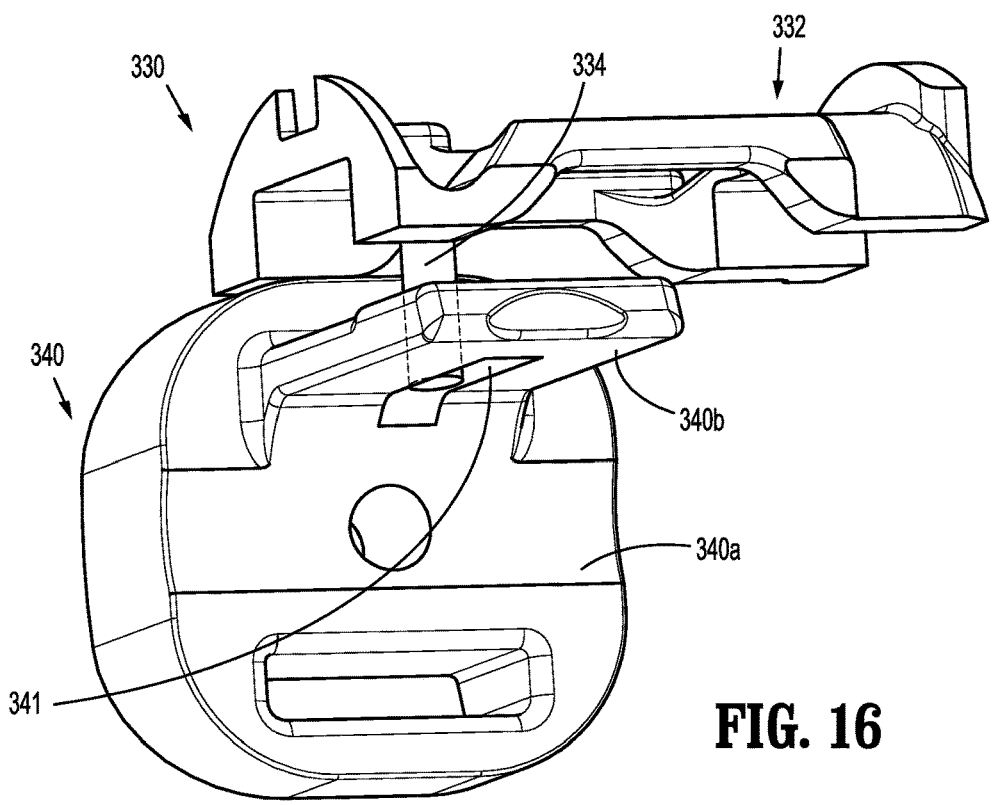
FIG. 16 is a perspective view of a retaining mechanism according to still another embodiment of the present disclosure.

Turning to FIG. 16, a retaining mechanism according to another embodiment of the present disclosure is shown as retaining mechanism 330. The retaining mechanism 330 includes a first mounting half 332 and a first button member 340 moveably positioned relative to the first mounting half 332. For simplicity, the retaining mechanism 330 will only be described as relates to the first button member 340. It is understood that the retaining mechanism 330 may include a second button member and second mounting half that are mirror images of the first button member 340 and the first mounting half 332. The first button member 340 of the retaining mechanism 330 is substantially similar to the first and second button members 240, 242 of the retaining mechanism 230 described above, and will only be described in detail as relates to the differences therebetween.

The first button member 340 of the retaining mechanism 330 includes an engagement portion 340a, and an attachment portion 340b extending from the engagement portion 340a. The attachment portion 340b of the first button member 340 defines a slot 341. The first mounting half 332 of the retaining mechanism 330 includes a pin 334. The first button member 340 is positioned relative to the first mounting half 332 such that the pin 334 is received within the slot 341 in the attachment portion 340b of the first button member 340. The pin 334 is configured to limit a distance the first button member 340 may travel outwardly, thereby limiting the travel of the first button member 340. In this manner, the first button member 340 of the retaining mechanism 330 remains secured to the adapter assembly (not shown), thereby preventing loss of the first button member 340 during cleaning and sterilizing of the adapter assembly.

Figure 17:
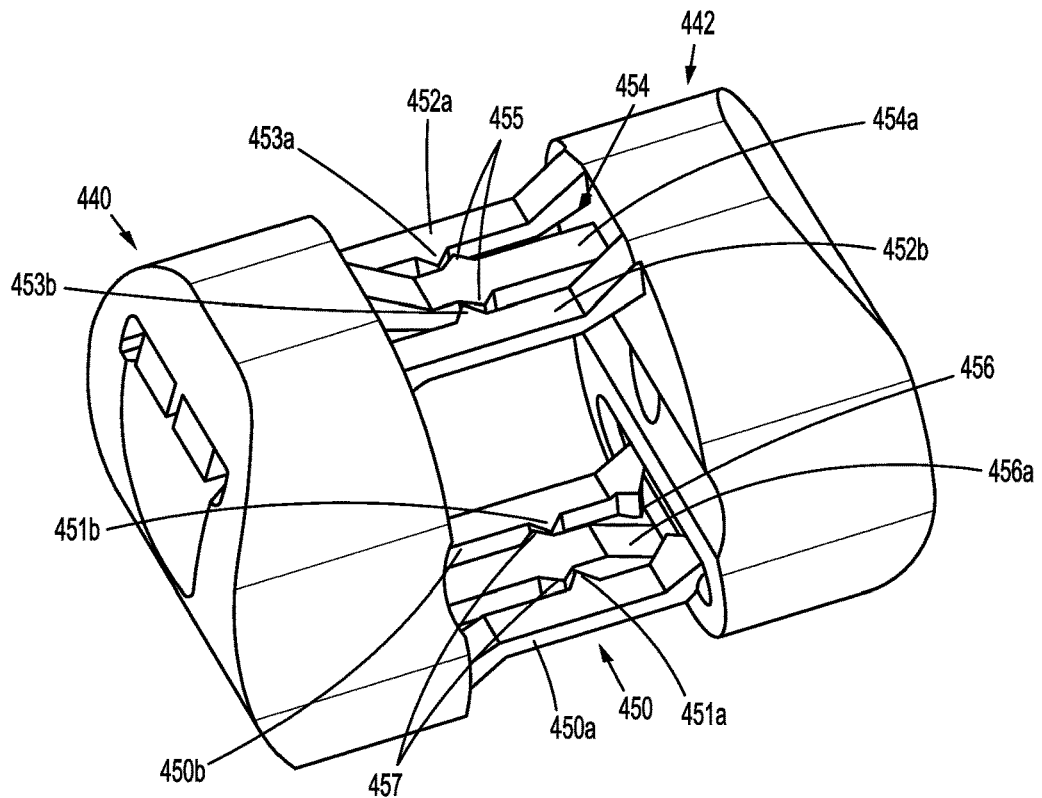
FIG. 17 is a perspective view of a retaining mechanism according to yet another embodiment of the present disclosure.

With reference now to FIG. 17, another retaining mechanism according to the present disclosure is shown generally as retaining mechanism 430. The retaining mechanism 430 is substantially similar to the retaining mechanisms 230, 330 described above, and will only be described in detail as relates to the differences therebetween.

The retaining mechanism 430 includes first and second button members 440, 442. Each of the first and second button members 440, 442 includes a first attachment portion 450, 452, respectively, and a second attachment portion 454, 456. The first attachment portions 450, 452 of the respective first and second button members 440, 442 each includes a pair of spaced apart elongate members 450a, 450b, 452a, 452b. Limiting features 451a, 451b, 453a, 453a extend inwardly from the respective paired spaced apart elongate members 450a, 450b, 452a, 452b. The second attachment portions 454, 456 of the first and second button members 440, 442 each include an elongate member 454a, 456a, respectively, configured to be received between the paired spaced apart elongate members 450a, 450b, 452a, 452b. Each of the elongate members 454a, 456a of the respective first and second button members 440, 442 includes a pair of outwardly extending limiting features 455, 457.

The first and second button members 440, 442 of the retaining mechanism 430 are disposed relative to each other such that the elongate member 456a of the second attachment portion 456 of the second button member 442 is slidingly received between the paired spaced apart elongate members 450a, 450b of the first attachment portion 450 of the first button member 440, and the elongate member 454a of the second attachment portion 454 of the first button member 440 is received between the paired spaced apart elongate members 452a, 452b of the second attachment portion 452 of the second button member 442.

The retaining mechanism 430 is configured to limit outward movement of the first and second button members 440, 442 relative to each other. More particularly, the pair of outwardly extending limiting features 455, 457 of the respective elongate members 454a, 456a of the second attachment portions 454, 456, respectively, of the respective first and second button members 440, 442 engage the respective limiting members 453a, 453a, 451a, 451b extend inwardly from the respective paired spaced apart elongate members 452a, 452b, 450a, 450b of first attachment portions 452, 450 of the second and first button members 442, 440 as the first and second button members 440, 442 are moved outwardly away from each other to retain the first and second button member 440, 442 within an adapter assembly (not shown).

Figure 18:
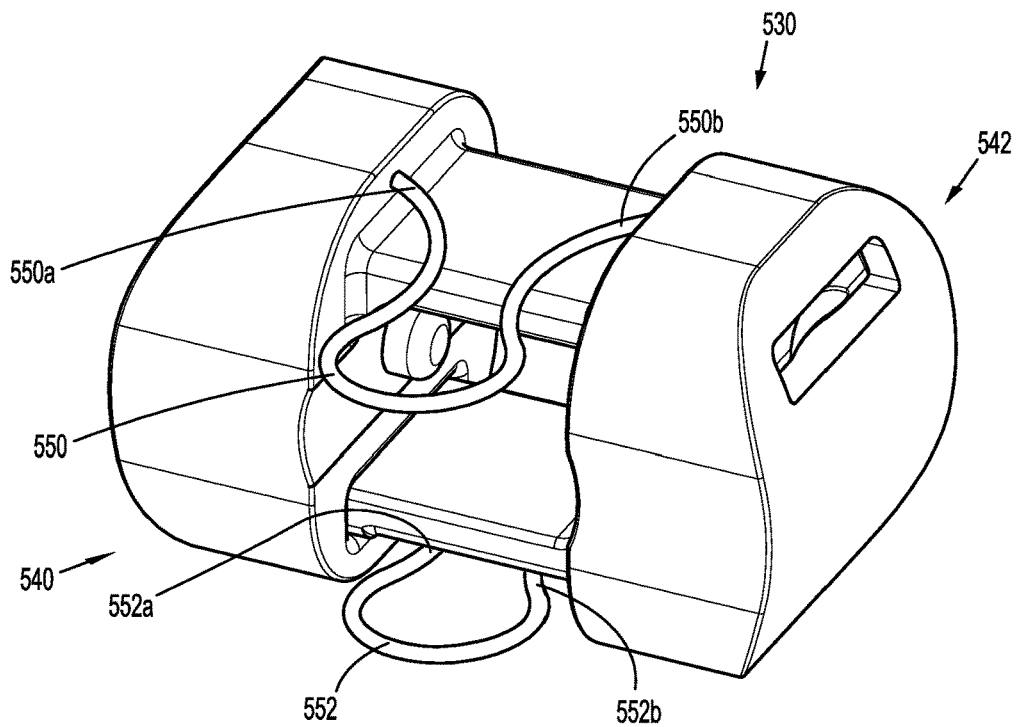
FIG. 18 is a perspective view of a retaining mechanism according to still yet another embodiment of the present disclosure, in a lock position.
Figure 19:
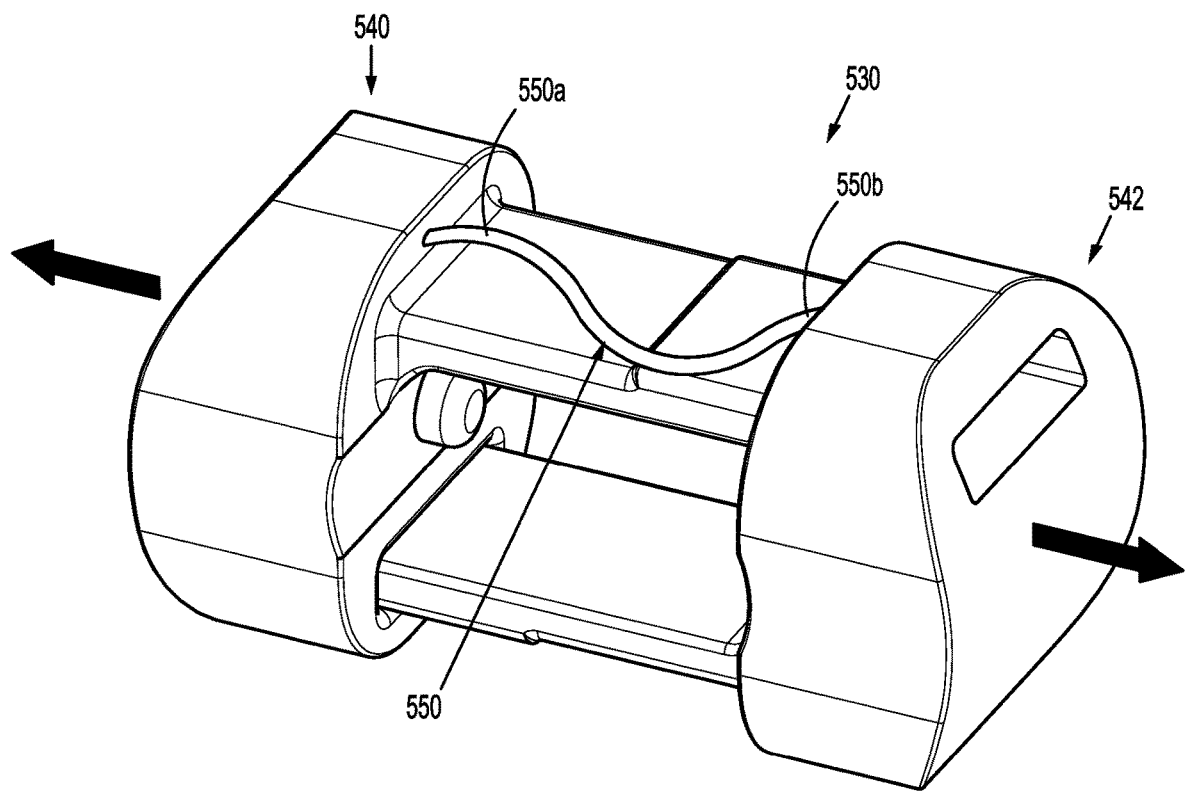
FIG. 19 is a perspective view of the retaining mechanism shown in FIG. 18, in a release position.

With reference to FIGS. 18 and 19, yet another embodiment of a retaining mechanism is shown generally as retaining mechanism 530. The retaining mechanism 530 is substantially similar to the retaining mechanisms 230, 330, 430 described above and will only be described as relates to the differences therebetween.

First and second button members 540, 542 of the retaining mechanism 530 are maintained relative to each other by first and second clip members 550, 552. The first and second clip members 550, 552 each include an end 550a, 552a that is secured to an engagement portion 550a of the first button member 550 and a second end 550b, 552b that is secured to an engagement portion 552 of the second button member 552. As shown, the first and second clip members 550, 552 are substantial identical and include a horseshoe-shape (FIG. 18), however, the first and second clip members 550, 552 may be different and may include other configurations, e.g., coil spring, accordion. The first and second clip members 550, 552 are configured to be deformed to permit the first and second button members 540, 542 to be moved outwardly relative to each other. The first and second clip members 550, 552 limit the distance the first and second button members 540, 542 travel outwardly relative to each other, i.e., tether the first and second button members 540, 542 to each other.

Figure 20:
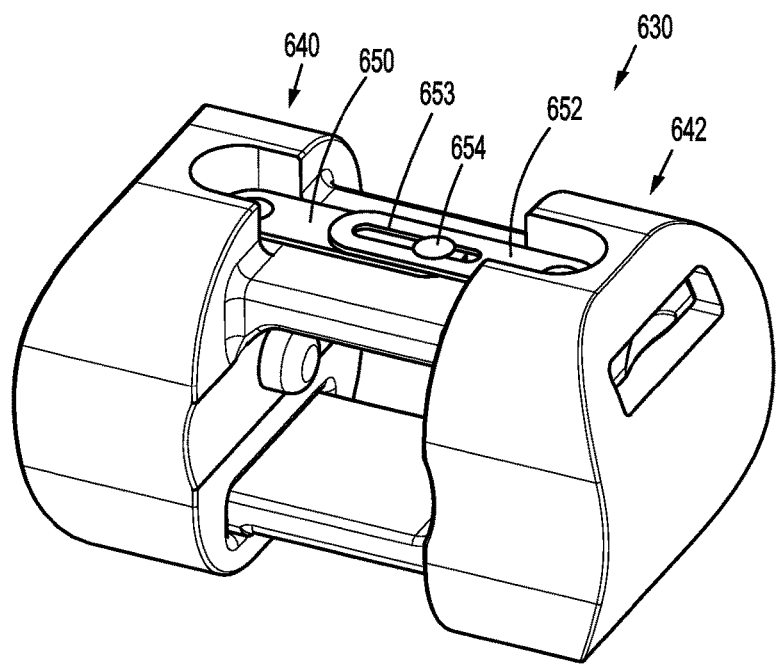
FIG. 20 is a perspective view of a retaining mechanism according to still yet another embodiment of the present disclosure, in a lock position.
Figure 21:
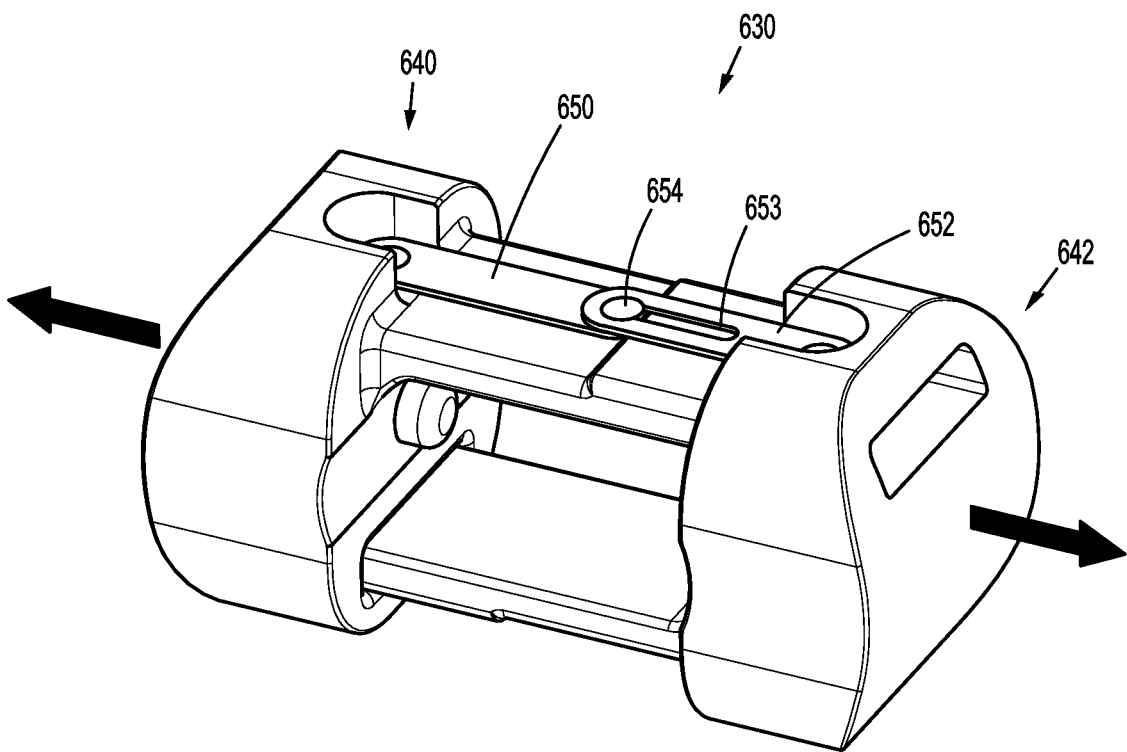
FIG. 21 is a perspective view of the retaining mechanism shown in FIG. 20, in a release position.

With reference to FIGS. 20 and 21, still another embodiment of a retaining mechanism is shown generally as retaining mechanism 630. The retaining mechanism 630 is substantially similar to the retaining mechanisms 230, 330, 430, 530 described above and will only be described as relates to the differences therebetween.

The retaining mechanism 630 includes first and second button members 640, 642. The first and second button members 640, 642 each include a flange member 650, 652 extending inward from an engagement portion 640a, 642a of the respective first and second button members 640, 642. One of the flange members, e.g., flange member 650 that extends from the first button member 640, includes a pin or rivet 654, and the other of the flange members, e.g., flange member 652 that extends from the second button member 642, defines a slot 653. The pin 654 of the first button member 640 is received within the slot 653 of the second button member 642. The slot and pin configuration limits the outward movement of the first and second button members 640, 642 of the retaining mechanism 630 relative to each other.

Although shown with only one set of flange members 650, 652, it is envisioned that the retaining mechanism 630 may include a second set of flange members (not shown) on an opposite side of the first and second button members 640, 642.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described.

What is claimed is:

1. An adapter assembly for connecting a loading unit to a handle assembly, the adapter assembly comprising:
    an elongate body including an outer sleeve;
    a trocar assembly releasably securable with the elongate body, the trocar assembly including a trocar housing defining first and second openings; and
    a retaining mechanism configured to releasably secure the trocar assembly within the elongate body, the retaining mechanism including first and second button members configured for operable engagement by a user, the first and second button members are moveable between a lock position in which the trocar assembly is securely received with the outer sleeve and a cleanse position in which the first and second button members extend beyond the outer sleeve, wherein the first and second button members are secured directly to one another to maintain the first and second button members with the elongate body.

2. The adapter assembly of claim 1, wherein the first and second button members are secured to one another with a pin and slot configuration.

3. The adapter assembly of claim 1, wherein the retaining mechanism further includes a first mounting member, the first mounting member including a pin and the first button member defining a slot, wherein the pin of the first mounting member is received in the slot in the first button member.

4. The adapter assembly of claim 3, wherein the retaining mechanism includes a second mounting member, the second mounting member including a pin and the second button member defining a slot, wherein the pin of the second mounting member is received in the slot in the second button member.

5. The adapter assembly of claim 1, wherein each of the first and second button members includes a first attachment portion and a second attachment portion, the first attachment portion of the first button member engaging the second attachment portion of the second button member and the first attachment portion of the second button member engaging the second attachment portion of the first button member.

6. The adapter assembly of claim 5, wherein each of the first and second attachment portions of each of the first and second button members includes at least one limiting feature.

7. The adapter assembly of claim 1, wherein the first and second button members are secured to one another with a clip member.

8. The adapter assembly of claim 7, wherein the clip member includes a substantial horseshoe-shape.

9. The adapter assembly claim 7, wherein the clip member includes first and second portions, the first portion being secured to the first button member and the second portion being secured to the second button member.

10. The adapter assembly of claim 1, wherein the retaining mechanism further includes a first flange extending from the first button member and a second flange extending from the second button member, the first flange including a rivet and the second flange defining a slot, wherein the rivet is received in the slot to maintain the first and second button members relative to each other.

11. An adapter assembly for connecting a loading unit to a handle assembly, the adapter assembly comprising:
an outer sleeve;
a trocar assembly releasably securable with the outer sleeve, the trocar assembly including a trocar housing defining first and second openings; and
a retaining mechanism configured to releasably secure the trocar assembly within the elongate body, the retaining mechanism including first and second button members configured for operable engagement by a user, the first and second button members moveable between a lock position in which the trocar assembly is securely received with the outer sleeve and a cleanse position in which the first and second button members extend beyond the outer sleeve, wherein the retention mechanism includes a connection mechanism for securing the first button member to the second button member to maintain the first and second button members with the elongate body.

12. The adapter assembly of claim 11, wherein the first and second button members are secured to one another with a pin and slot configuration.

13. The adapter assembly of claim 11, wherein the retaining mechanism further includes a first mounting member, the first mounting member including a pin and the first button member defining a slot, wherein the pin of the first mounting member is received in the slot in the first button member.

14. The adapter assembly of claim 13, wherein the retaining mechanism includes a second mounting member, the second mounting member including a pin and the second button member defining a slot, wherein the pin of the second mounting member is received in the slot in the second button member.

15. The adapter assembly of claim 11, wherein each of the first and second button members includes a first attachment portion and a second attachment portion, the first attachment portion of the first button member engaging the second attachment portion of the second button member, and the first attachment portion of the second button member engaging the second attachment portion of the first button member.

16. The adapter assembly of claim 15, wherein each of the first and second attachment portions of each of the first and second button members includes at least one limiting feature.

17. The adapter assembly of claim 11, wherein the first and second button members are secured to one another with a clip member.

18. The adapter assembly of claim 17, wherein the clip member includes a substantial horseshoe-shape.

19. The adapter assembly claim 17, wherein the clip member includes first and second portions, the first portion being secured to the first button member and the second portion being secured to the second button member.

20. The adapter assembly of claim 11, wherein the retaining mechanism further includes a first flange extending from the first button member and a second flange extending from the second button member, the first flange including a rivet and the second flange defining a slot, wherein the rivet is received in the slot to maintain the first and second button members relative to each other.

* * * * *